US006558361B1

(12) United States Patent
Yeshurun

(10) Patent No.: US 6,558,361 B1
(45) Date of Patent: May 6, 2003

(54) SYSTEMS AND METHODS FOR THE TRANSPORT OF FLUIDS THROUGH A BIOLOGICAL BARRIER AND PRODUCTION TECHNIQUES FOR SUCH SYSTEMS

(75) Inventor: Yehoshua Yeshurun, Haifa (IL)

(73) Assignee: Nanopass Ltd., Nalareth Illit (IL)

( * ) Notice: Subject to any disclaimer, the term of this patent is extended or adjusted under 35 U.S.C. 154(b) by 259 days.

(21) Appl. No.: 09/589,369

(22) Filed: Jun. 8, 2000

(51) Int. Cl.[7] .............................................. A61M 37/00
(52) U.S. Cl. ...................................... 604/272; 604/274
(58) Field of Search ........................... 604/22, 191, 264, 604/272, 274

(56) References Cited

U.S. PATENT DOCUMENTS

| 3,964,482 A | * | 6/1976 | Gerstel et al. ............... 424/449 |
| 5,697,901 A | * | 12/1997 | Eriksson ....................... 514/44 |
| 6,256,533 B1 | * | 7/2001 | Yuzhakov et al. ............. 604/20 |

FOREIGN PATENT DOCUMENTS

| WO | WO99/64580 | 12/1999 |
| WO | WO00/74763 | 12/2000 |
| WO | WO00/74764 | 12/2000 |
| WO | WO00/74766 | 12/2000 |

* cited by examiner

Primary Examiner—J. Casimer Jacyna
(74) Attorney, Agent, or Firm—Mark M. Friedman

(57) ABSTRACT

A device for the transport of fluids through a biological barrier includes a number of microneedles projecting from the front face of a substrate. A conduit is associated with each of the microneedles to provide a fluid flow path for transport of fluid through a hole in the biological barrier formed by the corresponding microneedle. Each of the microneedles is configured to provide a penetrating tip, and each conduit terminates at an opening which is proximal with respect to the microneedle tip. Also described are microneedle-based devices with integrated MEMS pumping configurations for withdrawal and/or delivery of fluids, and remote healthcare systems based on such devices.

14 Claims, 28 Drawing Sheets

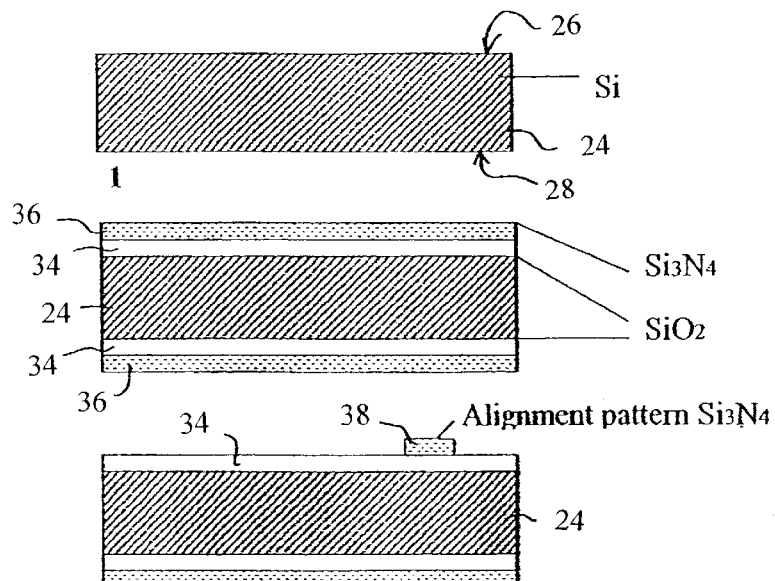
Fig. 3A
Fig. 3B
Fig. 3C
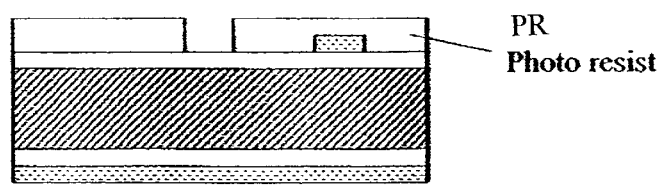
Fig. 3D
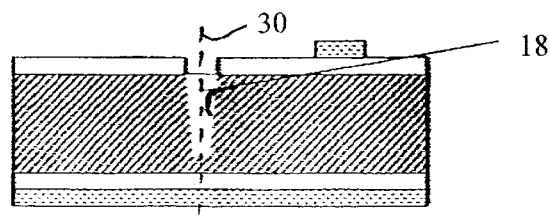
Fig. 3E
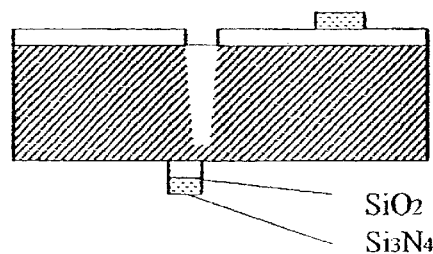
Fig. 3F
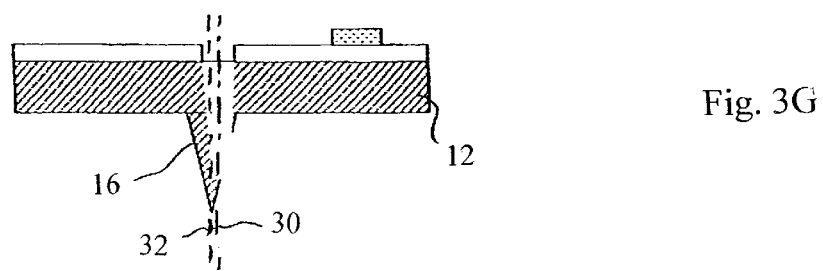
Fig. 3G LPCVD deposit of Nitride after masking was exposed and removed Oxidation substrate Etching part after masking exposed and removed Deposit spacer layer 2 micron of PSG Photo resist pattern and etch base windows Metal coating Remove resist and spacer layer Fig. 10A 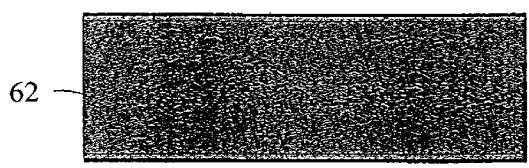 Fig. 10F 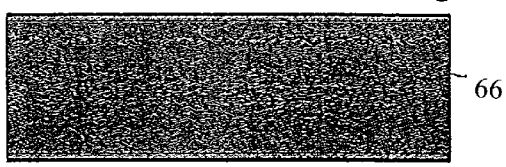
Fig. 10B 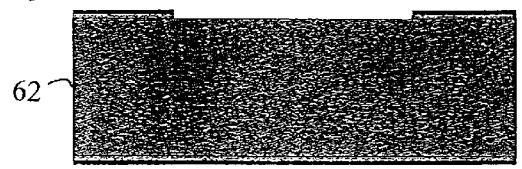 Fig. 10G 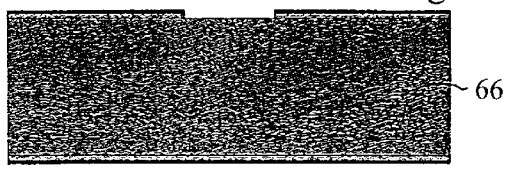
Fig. 10C 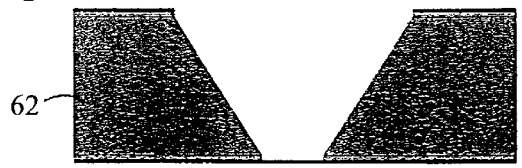 Fig. 10H 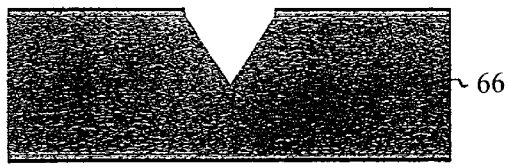
Fig. 10D 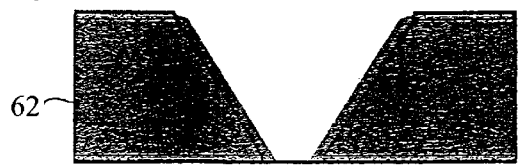 Fig. 10I 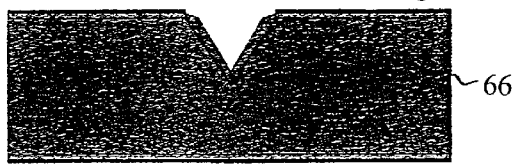
Fig. 10E 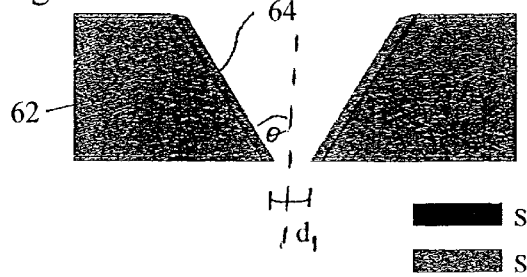 Fig. 10J 
■ Silicon Nitride
▨ Silicon Oxide
▧ Silicon 62
66

70
62
66

Silicon Oxide
Silicon
TiNi Alloy 70
72

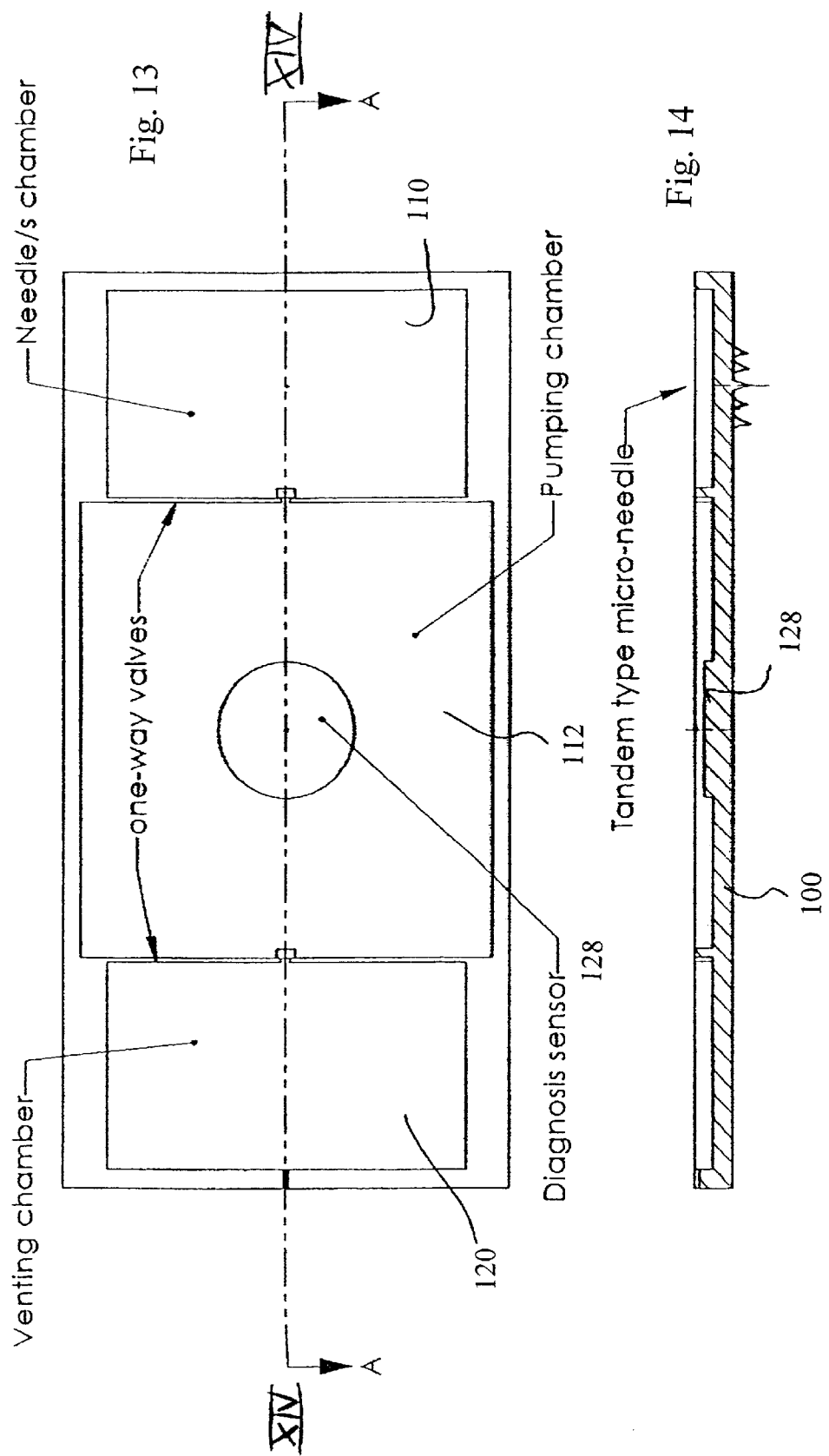

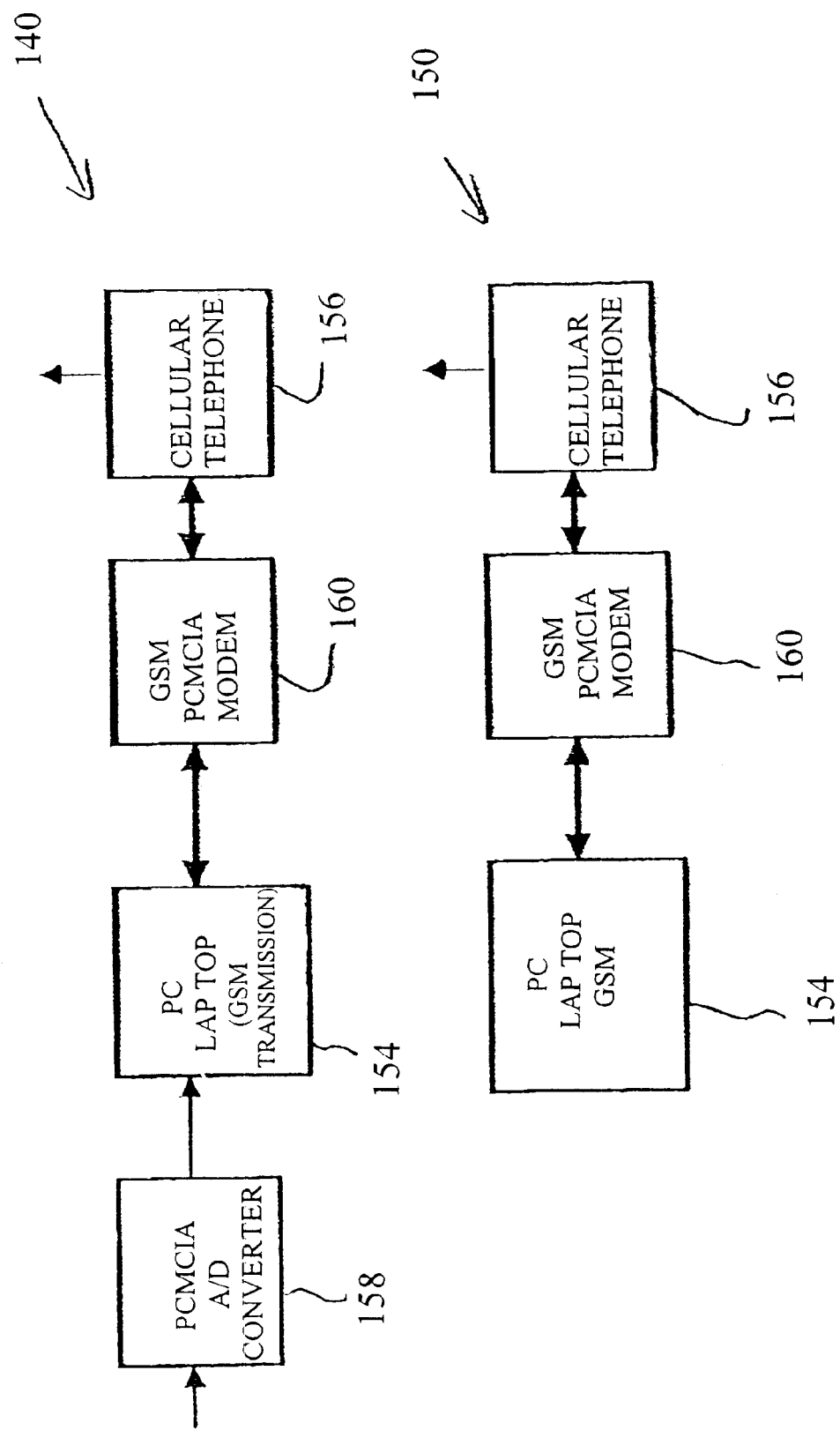

SYSTEMS AND METHODS FOR THE TRANSPORT OF FLUIDS THROUGH A BIOLOGICAL BARRIER AND PRODUCTION TECHNIQUES FOR SUCH SYSTEMS

FIELD AND BACKGROUND OF THE INVENTION

The present invention relates to drug delivery and diagnostic sampling and, in particular, it concerns systems and methods for the transport of fluids through a biological barrier and production techniques for such systems.

Various techniques are known for drug delivery. A first set of techniques employ oral delivery in the form of pills or capsules. Many drugs cannot, however, be effectively delivered orally due to degradation in the digestive system, poor absorption and/or elimination by the liver.

A second set of techniques deliver drugs directly across the dermal barrier using a needle such as with standard syringes or catheters. These techniques, however, require administration by one trained in their use, and often cause unnecessary pain and/or local damage to the skin. The withdrawal of body fluids for diagnostic purpose using a conventional needle suffers from the same disadvantages. The use of a conventional needle is also undesirable for long term, continuous drug delivery or body fluid sampling.

An alternative delivery technique employs a transdermal patch, usually relying on diffusion mechanisms. The usefulness of transdermal patches, however, is greatly limited by the inability of larger molecules to penetrate the dermal barrier. Transdermal patches are not usable for diagnostic purposes.

Many attempts have been made to develop alternative devices for active transfer of pharmaceutical materials, or for biological sampling, across the dermal barrier. For example, U.S. Pat. No. 5,250,023 to Lee et al. discloses a drug delivery device which includes a plurality of non-hollow microneedles having a diameter of 50–400 micron which perforate the skin to facilitate transfer of larger molecules through the dermal barrier. The microneedles are disclosed as being made of stainless steel.

More recently, much research has been directed towards the development of microneedles formed on chips or wafers by use of micro-machining techniques. This approach promises the possibility of producing numerous, very small needles which are sufficient to form small perforations in the dermal barrier, thereby overcoming the molecular size limitations of conventional transdermal patches, while being safe for use by unqualified personnel. Examples of such work may be found in PCT Publication No. WO 99/64580 to Georgia Tech Research Corp., as well as in the following scientific publications: "Micro machined needles for the transdermal delivery of drugs", S. H. S. Henry et al. (MEMS 98, Heildelberg, Germany, January 1998); "Three dimensional hollow micro needle and microtube arrays", D. V. McAllister et al. (Transducer 99, Sendai, Japan, June 1999); "An array of hollow micro-capillaries for the controlled injection of genetic materials into animal/plant cells", K. Chun et al. (MEMS 99, Orlando, Fla., January 1999); and "Injection of DNA into plant and animal tissues with micromechanical piercing structures", W. Trimmer et al. (IEEE workshop on MEMS, Amsterdam, January 1995). The more recent of these references, namely, the Georgia Tech application and the Chun et al. reference, disclose the use of hollow microneedles to provide a flow path for fluid flow through the skin barrier.

While hollow microneedles are potentially an effective structure for delivering fluids across the dermal barrier, the structures proposed to-date suffer from a number of drawbacks. Most notably, the proposed structures employ microneedles with flat hollow tips which tend to punch a round hole through the layers of skin. The punched material tends to form a plug which at least partially obstructs the flow path through the microneedle. This phenomenon is clearly visible in the scanning electron microscope (SEM) image identified as FIG. 11 of the Chun et al. reference and reproduced here as FIG. 1. This is particularly problematic where withdrawal of fluids is required since the suction further exacerbates the plugging of the hollow tube within the microneedle. The flat ended form of the needles also presents a relatively large resistance to penetration of the skin, reducing the effectiveness of the structure.

A further group of proposed devices employ microneedles formed by in-plane production techniques. Examples of such devices are described in U.S. Pat. No. 5,591,139 to Lin et al., U.S. Pat. No. 5,801,057 to Smart et al., and U.S. Pat. No. 5,928,207 to Pisano et al. The use of in-plane production techniques opens up additional possibilities with regard to the microneedle tip configuration. This, however, is at the cost of very limited density of microneedles (either a single microneedle or at most, a single row of needles), leading to corresponding severe fluid flow rate limitations. The very long proposed needle (about 3 mm) of Smart et al. suffers from an additional very high risk of needle breakage.

A further shortcoming of microneedle structures made by micromachining techniques is the brittleness of the resulting microneedles. Microneedles made from silicon or silicon dioxide are highly brittle. As a result, a significant proportion of the microneedles may fracture due to the stresses occurring during penetration, leaving fragments of the material within the tissue. Furthermore, oblique insertion by an unskilled person could lead to fracture of a very large proportion of the needles, resulting in malfunction of the device.

There is therefore a need for devices and methods based on micro-machining technology for the transport of fluids through the dermal barrier which would reduce or eliminate the problems of blockage by the layers of skin. I would also be highly advantageous to provide devices of this type with highly flexible microneedles to avoid leaving fragments of the microneedles within the skin tissue. Finally, there is a need for practical devices and corresponding systems for implementing diagnosis and treatment of various conditions based on such technology.

SUMMARY OF THE INVENTION

The present invention provides devices and methods for the transport of fluids through a biological barrier and production techniques for such devices.

According to the teachings of the present invention there is provided, a device for the transport of fluids through a biological barrier, the device comprising: (a) a substrate defining a substantially planar front face of the device; (b) a plurality of microneedles projecting from the substantially planar front face, each of the microneedles having a maximum width dimension measured parallel to the front face of no more than about 400 µm and a maximum height dimension measured perpendicular to the front face of no more than about 2 mm; and (c) a conduit associated with each of the microneedles and extending through at least part of the substrate, each of the conduits being configured to provide a fluid flow path for transport of fluid through a hole in the biological barrier formed by the corresponding microneedle, wherein each of the microneedles is configured to provide a penetrating tip, the conduit terminating at an opening proximal with respect to the non-hollow penetrating tip.

According to a further feature of the present invention, each of the microneedles is formed as a conical pyramid having a first conical angle and terminating at an apex, and wherein the conduit is formed as a bore intersecting the conical pyramid not at the apex.

According to a further feature of the present invention, each of the microneedles is formed as a hollow tube terminating in a beveled end, a distal extreme of the beveled end serving as the penetrating tip.

According to a further feature of the present invention, the hollow tube has a substantially conical external shape. According to an alternative feature of the present invention, the hollow tube has a substantially cylindrical external shape.

According to a further feature of the present invention, at least an outer surface of the microneedles is formed from metallic material.

According to a further feature of the present invention, at least an outer surface of the microneedles is formed from a super-elastic alloy.

According to a further feature of the present invention, each of the microneedles has a maximum height dimension of no more than about 200 $\mu$m.

According to a further feature of the present invention, the plurality of microneedles is implemented as a two-dimensional array including at least 20 microneedles.

There is also provided according to the teachings of the present invention, a method for producing a device for the transport of fluids through a biological barrier, the method comprising: (a) providing a substrate having first and second parallel outward-facing surfaces; (b) processing the substrate so as to form a plurality of bores extending into the substrate from the first surface, each of the bores being substantially symmetrical about a central bore-axis; and (c) processing the substrate so as to remove at least part of the second surface in such a manner is to leave a plurality of conical projections projecting from a remaining thickness of the substrate, each of the conical projections being substantially symmetrical about a central cone-axis, wherein the bores and the conical projections are configured such that each of the bores intersects an external surface of a corresponding one of the conical projections, the bore-axis and the cone-axis being non-coincident.

According to a further feature of the present invention, each of the conical projections terminates at an apex, each of the bores being configured to intersect the corresponding conical projection without removing the apex.

According to a further feature of the present invention, a layer of metallic material is deposited over at least the conical projections.

According to a further feature of the present invention, a layer of a super-elastic alloy is deposited over at least the conical projections.

According to a further feature of the present invention, material of the substrate is removed from within the layer of super-elastic alloy so as to leave conical projections formed substantially exclusively from the layer of a super-elastic alloy.

There is also provided according to the teachings of the present invention, a method for producing a device for the transport of fluids through a biological barrier, the method comprising: (a) providing a substrate; (b) processing the substrate so as to form a plurality of hollow microneedles projecting from a remaining thickness of the substrate, each of the hollow microneedles being substantially symmetrical about a central needle-axis; and (c) eroding part of the hollow microneedles in a manner asymmetric with respect to the needle-axis so as to form beveled-ended hollow microneedles.

According to a further feature of the present invention, the eroding is performed by ion milling.

According to a further feature of the present invention, the eroding is performed by sand blasting.

According to a further feature of the present invention, a layer of metallic material is deposited over at least the beveled-ended hollow microneedles.

According to a further feature of the present invention, a layer of a super-elastic alloy is deposited over at least the beveled-ended hollow microneedles.

According to a further feature of the present invention, material of the substrate is removed from within the layer of super-elastic alloy so as to leave beveled-ended hollow microneedles formed substantially exclusively from the layer of a super-elastic alloy.

BRIEF DESCRIPTION OF THE DRAWINGS

The invention is herein described, by way of example only, with reference to the accompanying drawings, wherein:

FIGS. 3A–3G are schematic cross-sectional views illustrating stages in a first technique according to the present invention for the production of a microneedle structure;

FIG. 13 is a schematic plan view of a wafer from the device of FIG. 11;

FIG. 14 is a schematic cross-sectional view taken along the line XIV—XIV of FIG. 11;

FIG. 27 is a block diagram illustrating a communications system suitable for use in the system of FIG. 26.

DESCRIPTION OF THE PREFERRED EMBODIMENTS

Figure 1:
FIG. 1 is a SEM view of prior art hollow microneedles corresponding to FIG. 11 of the aforementioned Chun et al. reference.
Figure 2:
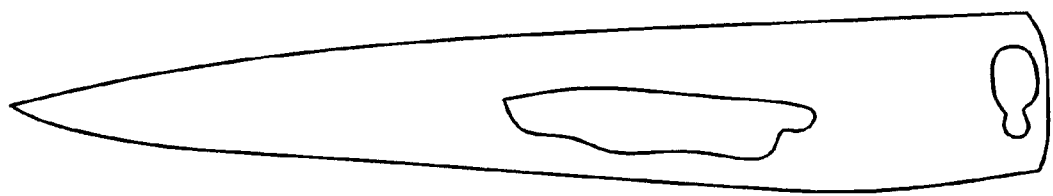
FIG. 2 is a schematic isometric representation of a microneedle point structure according to the teachings of the present invention.

The present invention provides devices and methods for the transport of fluids through a biological barrier and production techniques for such devices.

The principles and operation of devices according to the present invention may be better understood with reference to the drawings and the accompanying description.

Before addressing specific features of the present invention in detail, it will be useful to identify a number of distinct aspects of the invention to be discussed below. Firstly, with reference to FIGS. 2–10, various particularly preferred microneedle structures and corresponding production techniques will be discussed. Then, various microneedle-based devices for transporting fluid across biological barriers will be discussed with reference to FIGS. 11–25. Finally, with reference to FIGS. 26 and 27, systems will be presented for allowing remote diagnosis and/or treatment in the absence of trained medical personnel.

It should be noted that these various aspects of the invention are not limited to use in combination. Thus, the preferred microneedle structures are considered to be extremely valuable for use in a wide range of applications not limited to the specific devices to be described herein. Similarly, the devices described may be implemented in certain cases using microneedle structures other than those of the present invention. Finally, the systems for remote diagnosis and/or treatment may, in certain cases, be implemented with devices other than those described herein. This notwithstanding, it is believed that the devices of the present invention are most advantageously implemented using the microneedle structures of the present invention. Similarly, it is believed that the effectiveness of the remote healthcare systems described is greatly enhanced by use of the various devices and/or microneedle structures disclosed herein.

With this in mind, we turn now to the specific features of the present invention.

Microneedle Structures

Referring now to the drawings, FIGS. 2–10 relate to particularly preferred microneedle structures, constructed and operative according to the teachings of the present invention, and corresponding production techniques.

In general terms, a first aspect of the present invention provides a device for the transport of fluids through a biological barrier which employs microneedles with a tip structure which helps to prevent plugging of the microneedles during insertion. This is achieved primarily by providing an asymmetric tip with a non-hollow penetrating portion which extends beyond a fluid transfer aperture. This class of structures is epitomized by the beveled-end microneedle form illustrated in FIG. 2. In addition to avoiding plugging of the needle and facilitating withdrawal and delivery of fluids across a biological barrier, the shape illustrated also significantly increases the open area presented by the hollow tube, thereby dramatically increasing rates of fluid flow which can be achieved.

In conceptual terms, these structures are analogous to the beveled ends of conventional syringe needles which are known to be effective at penetrating tissue without becoming blocked. Such asymmetrical structures, however, are not readily achieved at the dimensions of microneedles addressed by the present invention. In particular, the techniques taught by the art to-date are not capable of producing structures with all array of out-of-plane microneedles projecting from the surface of a wafer which provide such asymmetric tip features.

Figure 4:
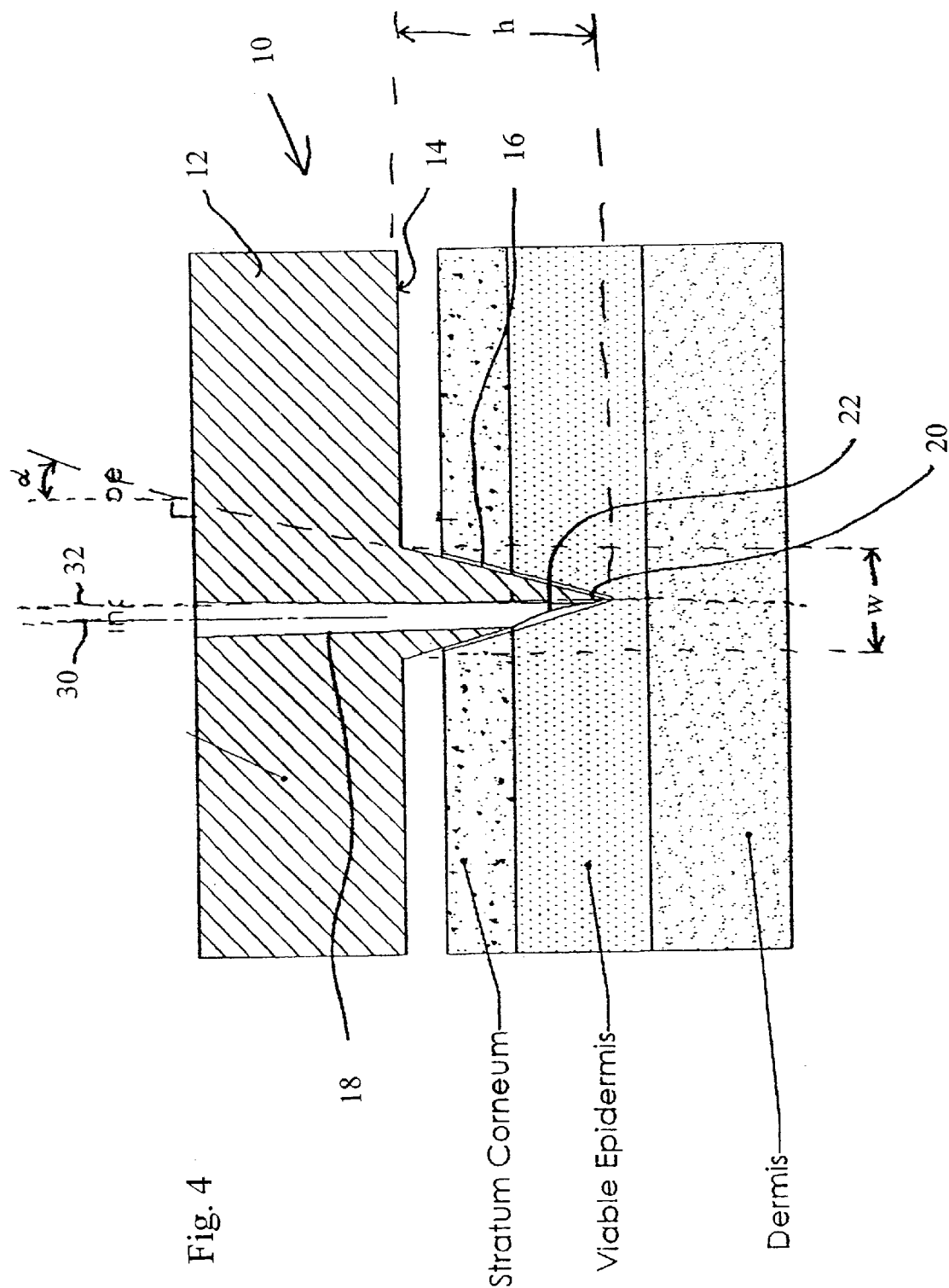
FIG. 4 is a schematic cross-sectional view illustrating the use of the microneedle structure produced by the technique of FIGS. 3A–3G for transferring fluid across a biological barrier.

Turning now to specific examples, FIG. 4 shows a microneedle structure, generally designated 10, including a substrate 12 defining a substantially planar front face 14 of the device. A plurality of microneedles 16 (only one of which is illustrated in this schematic representation) project from the front face 14. Each microneedle has a maximum width dimension w measured parallel to front face 14 of no more than about 400 $\mu$m and a maximum height dimension h measured perpendicular to the front face of no more than about 2 mm. A conduit 18, associated with each of microneedles 16, extends through at least part of substrate 12. Each conduit 18 is configured to provide a fluid flow path for transport of fluid through a hole in the biological barrier formed by the corresponding microneedle.

It is a particular feature of the microneedle structures according to this aspect of the present invention the each of microneedles 16 is configured to provide a non-hollow penetrating tip 20, the corresponding conduit 18 terminating at an opening 22 proximal with respect to the non-hollow penetrating tip 20. In this specific case, each microneedle 16 is formed as a conical pyramid having a conical angle α, and the corresponding conduit 18 is formed as a bore intersecting the conical pyramid not at its apex.

It will be readily appreciated that the microneedle structure described provides marked advantages over the flat-ended tube structures proposed by the prior art. The asymmetric tip configuration provides a clog-resistant structure which easily pierces the dermal barrier layer for controlled sampling and/or drug delivery in a minimally invasive, minimally damaging manner. This allows safe sampling of body fluids and/or drug delivery which can be performed by a patient or other untrained person and is relatively painless.

The relatively painless nature of the procedure may optionally be ensured by use of microneedles with a maximum height h chosen to allow penetration only to the stratum corneum (SC) and epidermis derma layers, thereby generally avoiding contact with nerves. This is also helpful for applications in which sampling of blood plasma rather than full blood is desired. For such applications, maximum height dimension h is preferably chosen to be no more than about 200 μm. For other applications in which deeper delivery or sampling is desired, longer microneedles are used to penetrate into the dermis. In this case, all or most pain can be avoided by employing narrow microneedles with a maximum width dimension of not more than 300 μm, and preferably not more than 200 μm. Optionally, anaesthetic and/or anticoagulants may be provided, for example as a coating to the needles, to reduce the amount of pain caused and/or to enhance operation of the device.

FIGS. 3A–3G illustrate stages in a technique according to the present invention for the production of a microneedle structure such as that of FIG. 4. In general terms, the method includes providing a substrate 24 (FIG. 3A) having first and second parallel outward-facing surfaces 26 and 28. Substrate 24 is then processed (FIGS. 3D and 3E) so as to form a plurality of bores 18 extending into the substrate from first surface 26. Each of bores 18 is substantially symmetrical about a central bore-axis 30. Substrate 24 is then processed (FIGS. 3F and 3G) so as to remove at least part of second surface 28 in such a manner as to leave a plurality of conical projections 16 projecting from a remaining thickness 12 of substrate 24. Each conical projection 16 is substantially symmetrical about a central cone-axis 32.

It is a particular feature of this particular production technique that bores 18 and conical projections 16 are configured such that each bore 18 intersects an external surface of a corresponding conical projection 16 with bore-axis 30 and cone-axis 32 being non-coincident. This provides the advantages of the asymmetric microneedle tip configuration described above.

In the particular example illustrated here, bore-axis 30 and cone-axis 32 are offset relative to each other sufficiently to ensure that each bore 18 intersects the corresponding conical projection 16 without removing its apex.

In an alternative implementation, the offset is smaller such that the bore overlaps the cone axis. This latter option produces a beveled tip effect (not shown).

It will be clear to one ordinarily skilled in the art that the above steps may readily be performed using a range of techniques and materials known in the field of micro-electromechanical systems (MEMS) production. Nevertheless, for completeness of presentation, further details of one specific implementation of the technique will now be presented by way of a non-limiting example.

Thus, in this example, wafer 24 may be a 300 μm silicon wafer polished on both sides. The wafer is then prepared by oxidation to produce a 1000 Å layer 34 of $SiO_2$ and by CVD (Chemical Vapor Deposition) of a 500 Å layer 36 of $Si_3N_4$ (FIG. 3B).

Lithography is then performed using a first mask and reactive ion etching (RIE) to form an alignment pattern 38 in the $Si_3N_4$. Although not part of the final structure, this alignment pattern is helpful in facilitating accurate alignment of the substrate for subsequent processing to be performed on opposite faces of the substrate.

Bores 18 are then formed by a second lithography step using a thick layer of photo resist (PR) and deep reactive ion etching (DRIE) to drill deep etch holes with a small conical angle, typically no more than about 5° and optionally approaching 0°, i.e., near cylindrical.

The next step is a second thermal oxidation of 2000 Å, to protect the bores from the front etching after being exposed.

Finally, a third Lithography step is performed with a third mask on surface 28 to produce a front side pattern defining the microneedle positions and a DRIE is used to produce the microneedles with a conical angle larger than that of bores 18, and lying in the range from about 5° to 27.35°.

It will be clear to one familiar with the field of MEMS that the specific materials, processes, and sequence of operations described in this specific example, and in all specific examples to be provided below, are not critical to the principles of the production technique. Thus, for example, the sequence of processing surfaces 26 and 28 may be reversed, and different solutions may be employed to facilitate correct relative alignment of the features formed from opposite surfaces of the wafer. Furthermore, the procedure may readily be adapted and/or supplemented for simultaneous production of various additional structural features which may be required in a device to be produced. The superfluous layer of oxide and the alignment pattern may clearly be removed if desired.

With regard to materials, it should be appreciated that wafer 24 may be any type of wafer suitable for use in MEMS manufacturing processes. Typical examples include, but are not limited to, silicon, gallium arsenide and various polymers such as polypropylene or PDMS. Combinations of semiconductor materials and polymers may also be used.

In many cases, the structure of FIG. 3G is further processed to provide additional desirable properties. Firstly, depending upon the wafer material, it may be preferable to coat at least the microneedles with a layer of bio-compatible material, typically a metal or metal alloy. For this purpose, a coating of about 2 μm titanium or stainless steel is typically sufficient. Thicker coating of at least 10–20 μm may also serve a structural safety function, tending to prevent fragments being left behind in the event that a brittle silicon needle might fracture.

According to a further preferred option, a layer of at least about 20 μm of a super-elastic alloy is deposited over at least the conical projections. An example of such an alloy is the range of NiTi alloys generally known as Nitinol. This offers a still further enhanced level of structural safety by providing a layer which is not prone to breaking or fracturing under a very wide range of operating conditions.

One preferred technique for forming the aforementioned metallic layers is sputtering. Sputtering techniques for applying NiTi are discussed in "Micromachining Process for thin film SMA actuators", Nakamura et al. (IEEE, February 1996). In order to achieve the required NiTi stoichiometry to produce super elastic properties, it is recommended to use a target such as micro needles pre-coated with a small amount of Ti or Ni. Increasing or decreasing the amount of Ni or Ti or any ternary element can result in a film transformation which is the basic principle of super alloy properties of any desired composition. The exact composition defines the temperature at which the super elastic behavior is exhibited. It has also been demonstrated that adjusting the target to substrate distance and sputtering gas pressure can change the NiTi stoichiometry from 47% to 52% Ti, while using a 50% Ti target. Such changing in the stoichiometry could produce super elastic properties at about room temperature. The deposited amorphous films must be annealed to achieve crystallinity. This annealing also promotes adhesion to the substrate through formation of a thin reaction layer (~40 nm). For equi-atomic NiTi, no change of thin film phase transformation as observed when annealing between 500–700° C., However Ti-rich film displays an increased transformation temperature while Ni-rich film displays a decreased temperature transformation. Thin film can recover from 6% strain at 600 MPa forces which is above the need for microneedle configurations.

In yet a further most preferred option, at least part of the substrate material is removed by etching away from under the metallic or super-elastic layer so as to leave conical projections 16 formed substantially exclusively from the layer of metallic material or super-elastic alloy. In the most highly preferred case of a super-elastic alloy, this results in a microneedle array which is effectively unbreakable under a wide range of conditions. This provides a highly valuable solution to the problem of fractured microneedles associated with the prior art, and provides a greatly improved level of safety against damage to the device or harm to the user if the needles are inserted improperly at an oblique angle to the skin.

Although shown here schematically with a single microneedle, the process described is clearly well suited to producing a one- or two-dimensional arrays of microneedles projecting from the surface of substrate 12 with any desired spacing, layout and dimensions. In fact, it is a particularly preferred feature of the microneedle structures of the present invention that a two-dimensional array including at least 20 microneedles is provided. More preferably, at least 50 microneedles are provided on each chip, and most preferably, at least 100. In many practical applications, large arrays of several hundreds, or thousands, of microneedles may be formed on a chip of less than 1 cm$^2$. The spacing between centers of adjacent microneedles is typically in the range of 2–4 times the maximum diameter of each needle.

Independent of the flexibility or otherwise of the microneedles themselves, it is generally preferable that the substrate itself is able to conform somewhat to the local contours of the skin against which it is placed. This may be achieved by using an inherently flexible substrate, such as a flexible polymer or flexible metallic materials. In the case of an inherently non-flexible substrate such as silicon, effective flexibility may be provided by mounting the wafer on a flexible layer (e.g., silicon rubber or a metallic layer) and etching the back side of the substrate in order to create "islands" of micro needles held together by the flexible layer.

Turning now to FIGS. 5A–5J and 6, there is shown a second production technique and corresponding microneedle structure according to the teachings of the present invention.

Figure 5A:
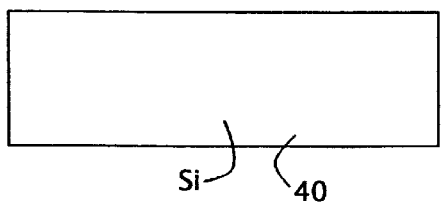
FIGS. 5A–5J are schematic cross-sectional views illustrating stages in a second technique according to the present invention for the production of a microneedle structure.
Figure 5B:
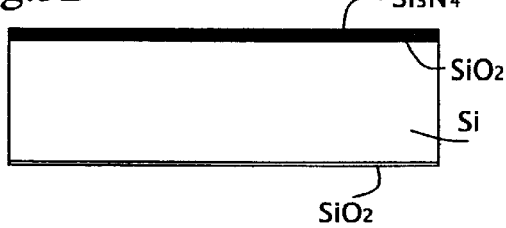
Figure 5C:
Figure 5D:
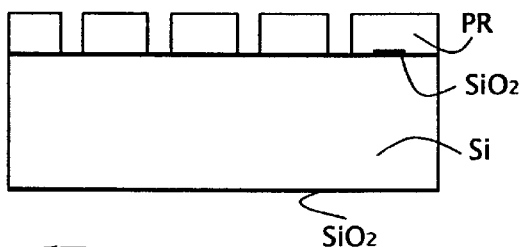
Figure 5E:
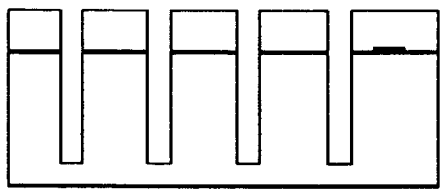
Figure 5F:
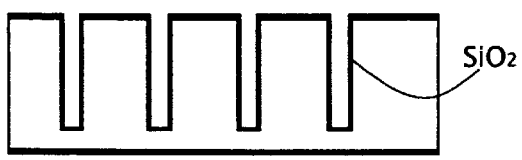
Figure 5G:
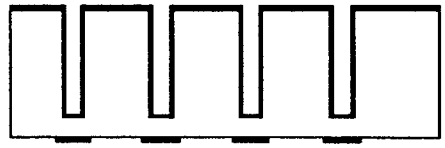
Figure 5H:
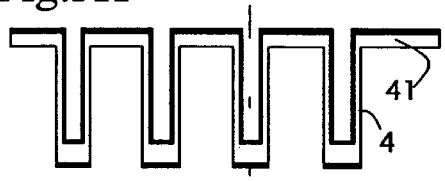
Figure 5I:
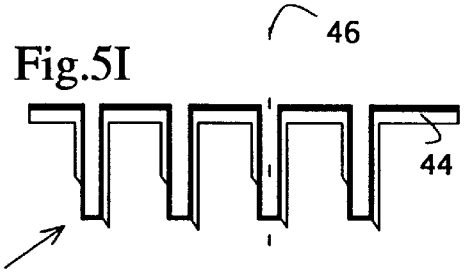
Figure 5J:
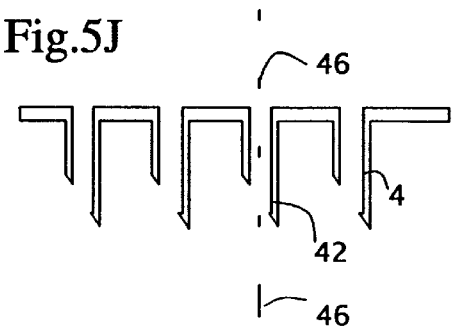
Figure 6:
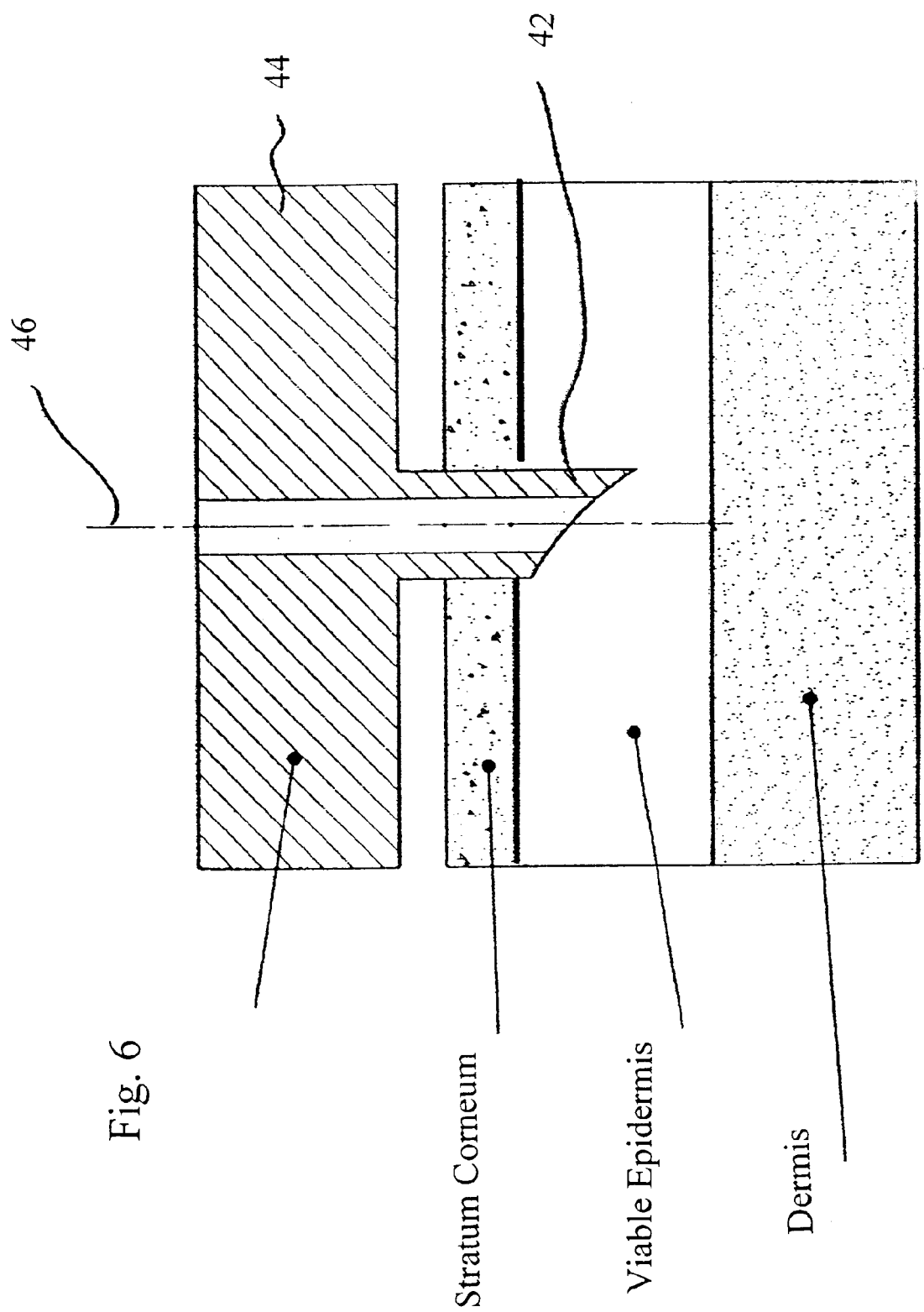
FIG. 6 is a view illustrating the use of the microneedle structure produced by the technique of FIGS. 5A–5E for transferring fluid across a biological barrier.
Figure 7A:
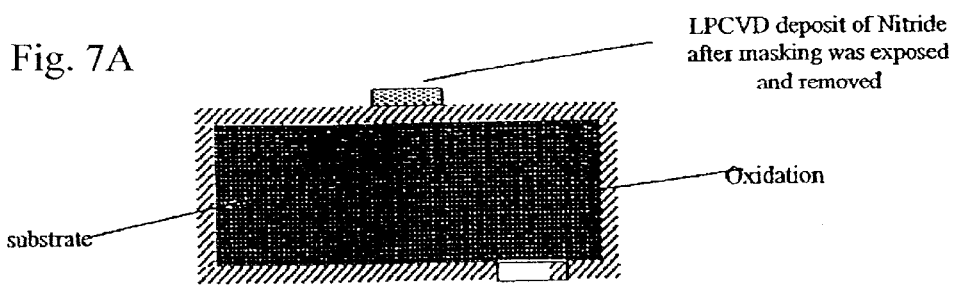
FIGS. 7A–7F are schematic cross-sectional views illustrating stages in a third technique according to the present invention for the production of a microneedle structure.
Figure 7B:
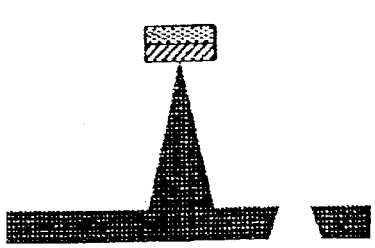
Figure 7C:
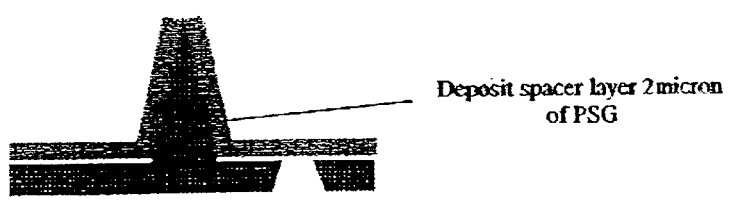
Figure 7D:
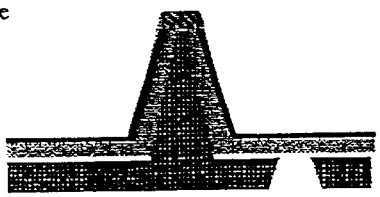
Figure 7E:
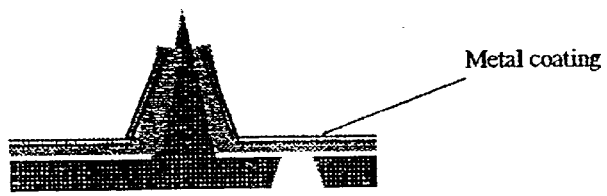
Figure 7F:
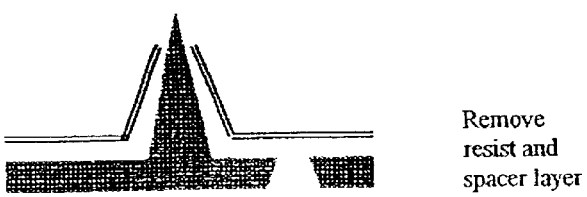

Generally speaking, this technique proceeds by processing a substrate 40 so as to form therein a plurality of hollow microneedles 42 projecting from a remaining thickness 44 of the substrate (FIGS. 5A–5H). Each hollow microneedle 42 is initially substantially symmetrical about a central needle-axis 46. In the case shown here, hollow microneedles 42 have a substantially cylindrical external shape, although conical microneedles may also be used. Part of each microneedle 42 is then eroded (FIG. 5I) in a manner asymmetric with respect to needle-axis 46 so as to form beveled-ended hollow microneedles (FIG. 5J). This leads to a microneedle structure as shown in FIG. 6 which very closely resembles the beveled form of a syringe needle.

This erosion process may be performed using a number of known techniques. Preferred, but non-limiting, examples of suitable techniques include ion milling, and sand blasting. Of these, ion milling is often preferred since it is generally more controllable. Optionally, in order to protect the lower portion of the microneedles, the etching process between FIGS. 5G and 5H may initially be performed to only part of the intended microneedle height, leaving only the tip portion exposed. In this case, the etching process is completed subsequent to the asymmetric erosion process (between FIGS. 5I and 5J) to form the remainder of the height of the microneedles.

Here too, the structure of FIG. 5J may optionally be coated, preferably with metallic material and most preferably with a super-elastic alloy, and at least part of the substrate material may be etched away from under the coating layer. In all other respects (materials, dimensions, layout, numbers etc.), this implementation is similar to the implementation of FIGS 3–4 described above.

Turning now to FIGS. 7A–7F and 8, there is shown a third production technique and corresponding microneedle structure according to the teachings of the present invention. This structure is particularly suited to fluid delivery through a biological barrier.

Figure 8:
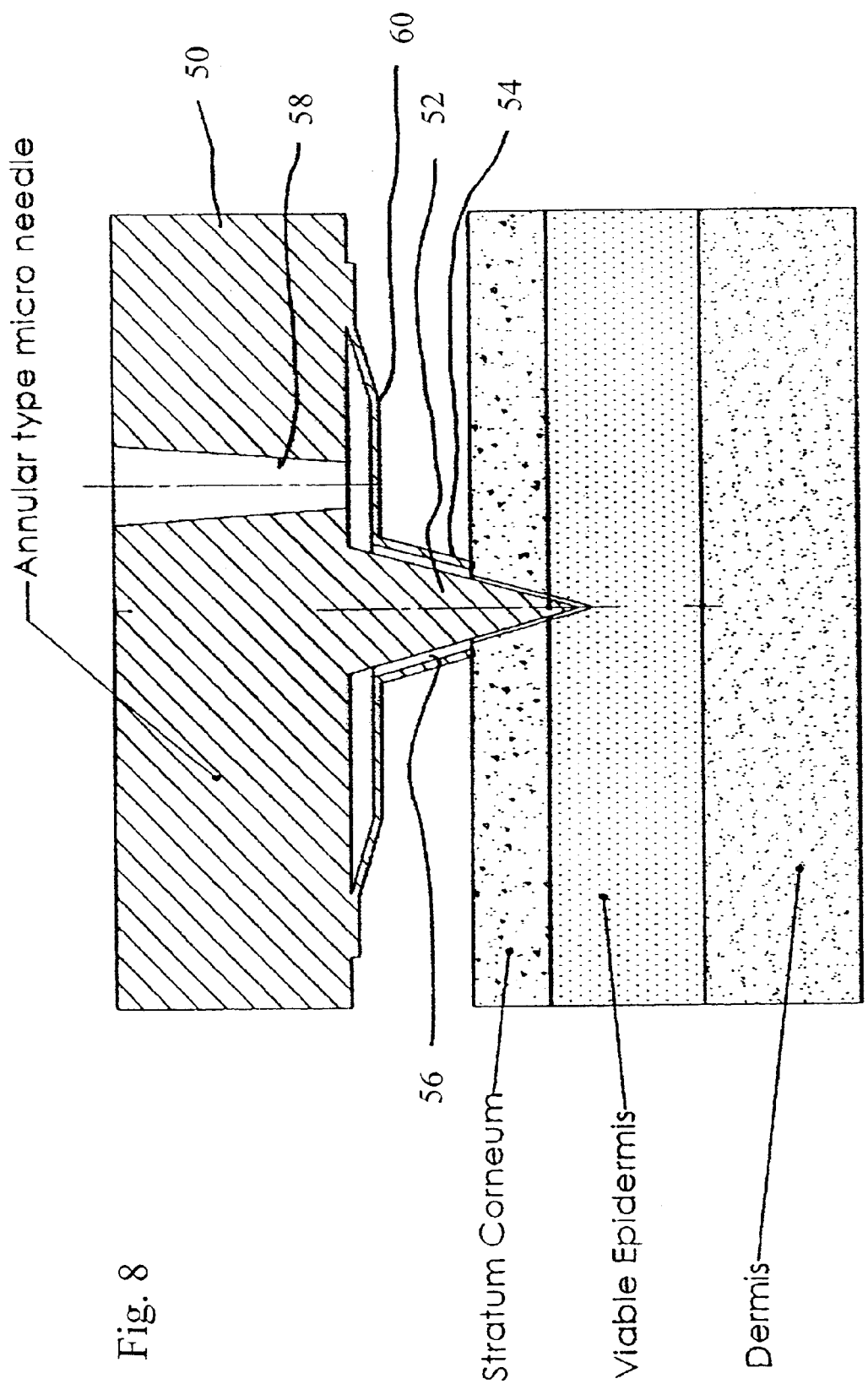
FIG. 8 is a schematic cross-sectional view illustrating the use of the microneedle structure produced by the technique of FIGS. 7A–7F for delivering fluid across a biological barrier.

Generally speaking, the microneedle structure of FIG. 8 includes a substrate 50 with a plurality of microneedles 52 projecting therefrom. In this case, microneedles 52 are typically solid microneedles having a maximum width dimension of no more than about 400 μm and a maximum height dimension of no more than about 2 mm. A plurality of hollow elements 54 are deployed substantially concentrically around, and slightly spaced from, corresponding microneedles 52 so as to define between them an annular passageway 56 extending along part of the height of the microneedle. At least one fluid flow channel 58, associated with substrate 50, is in fluid communication with each annular passageway 56 for supplying fluid to the annular passageways.

Preferably, hollow elements 54 are formed as part of a substantially continuous layer 60 overlying at least part of the substrate. In this case, at least part of fluid flow channel 58 advantageously passes between substrate 50 and layer 60. Here too, hollow elements 54 and layer 60 may advantageously be formed primarily from metallic material, and especially, from a super-elastic alloy.

A specific example of a production technique according to the present invention for forming the structure of FIG. 8 is illustrated in FIGS. 7A–7F. Specifically, a spacer layer of Phosphorous Silica Glass (PSG) is applied (FIG. 7C) after initial formation of an array of microneedles to define the relative spacing between a metal coating (FIG. 7E) and the microneedles of the substrate. Details of the various processes used in such techniques will be clear to one ordinarily skilled in the art.

The operation of this structure may be understood from FIG. 8. Unlike the previous examples in which the penetrating portion of a microneedle includes a conduit, penetration is preferably limited here to the solid distal portion of microneedles 52 such that hollow element 54 abuts the skin surface to form an annular seal around the point of penetration. Then, when fluid is supplied under pressure through annular passageway 56, the pressure forces the fluid through the hole in the dermal barrier made by microneedle 52.

This configuration is considered to be particularly valuable for fluid delivery across the dermal barrier since it requires only a very small depth of penetration into the dermal layers. Specifically, this configuration operates with penetration of less than 200 µm, and typically as little as about 50 µm, which is just sufficient to penetrate the stratum corneum.

Figure 9:
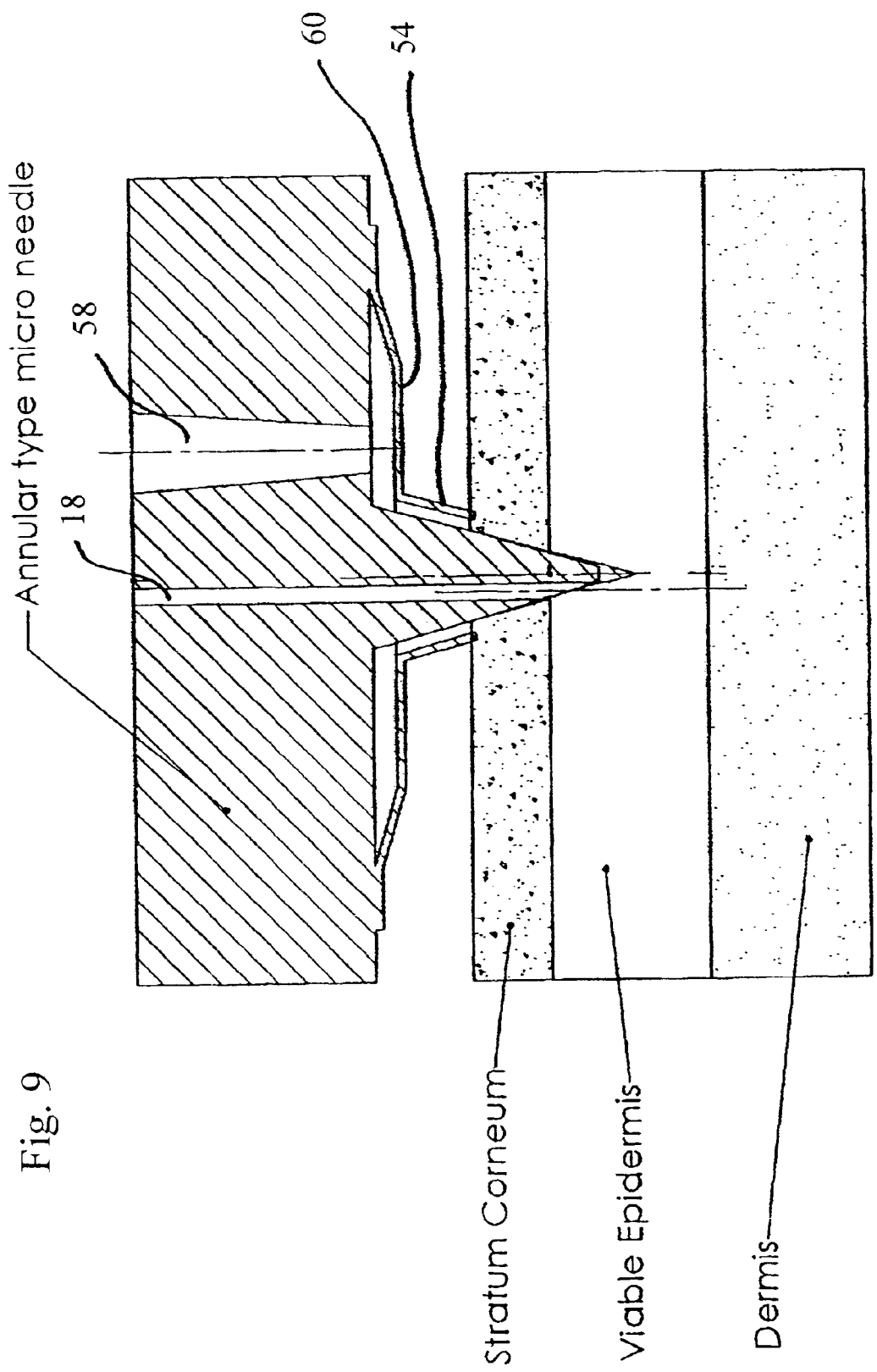
FIG. 9 is a schematic cross-sectional view illustrating a microneedle structure which combines the features of the structures of FIGS. 4 and 8.

Turning briefly to FIG. 9, it should be noted that the various structures described herein are not mutually exclusive. By way of example, FIG. 9 shows schematically a structure in which the concentric configuration of FIG. 8 is combined with the offset bore configuration of FIG. 4. Such a cofiguration may be useful to provide dual functionality for withdrawal and delivery of fluids to and from separate fluid reservoirs.

Figure 10K:
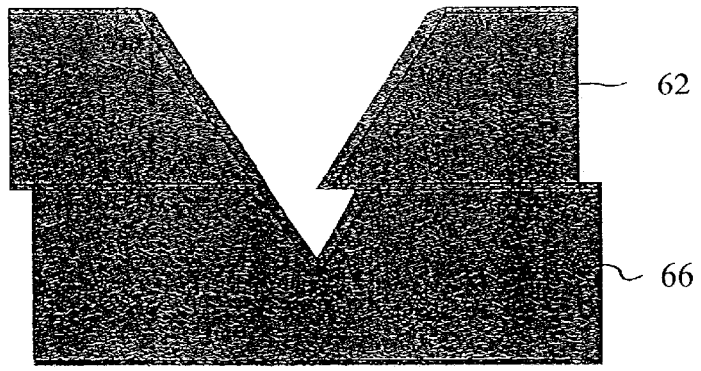
FIGS. 10A–10N are schematic cross-sectional views illustrating stages in a fourth technique according to the present invention for the production of a microneedle structure.
Figure 10L:
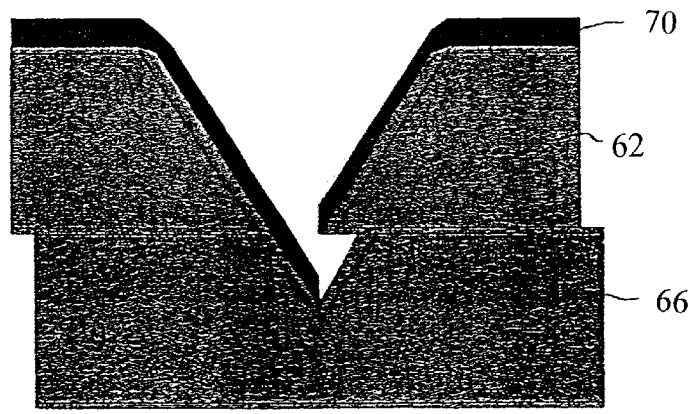
Figure 10M:
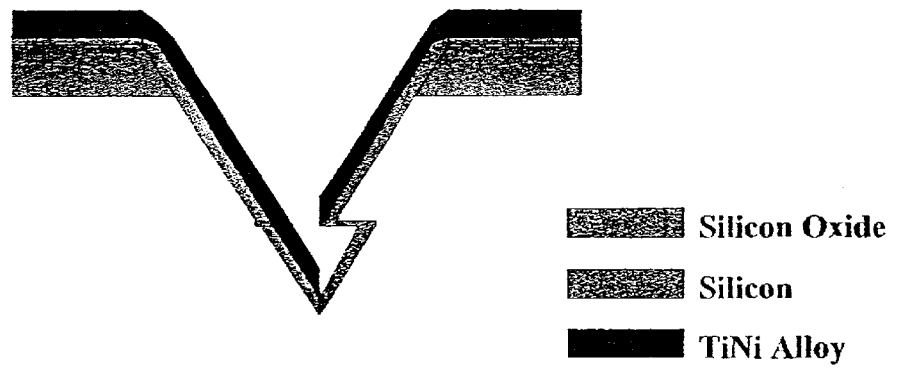
Figure 10N:
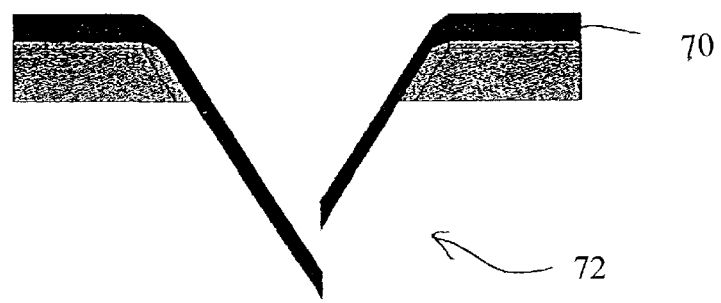

Finally with respect to the microneedle structures of the present invention, it should be noted that various alternative techniques may be used to implement the principles of the present invention. By way of example, FIGS. 10A–10N illustrate a production process based on combination of two separate wafers. Specifically, a first wafer 62 is etched to form a conical bore 64 having a first conical angle θ and a minimum bore diameter $d_1$ (FIGS. 10A–10E) and a second wafer 66 is etched to form a conical depression 68 having a conical angle φ and a maximum diameter $d_2$ (FIGS. 10F–10J). The wafers are then bonded together (FIG. 10K) and coated with a metal layer 70 (FIG. 10L). The substrate can then be etched away as shown in FIGS. 10M and 10N to reveal a microneedle structure 72.

Fluid Transport Devices

Turning now to the second aspect of the present invention, this relates to the overall design of various microneedle-based devices for the transport of fluids through a biological barrier. FIGS. 11–25 illustrate a number of examples of such devices.

In general terms, the devices of the present invention include a substrate 100 having a front surface 102 provided with an array of outwardly projecting microneedles 104 for penetrating into the biological barrier. Microneedles 104 each have a maximum width dimension of no more than about 400 µm and a maximum height dimension of no more than about 2 mm. Substrate 100 is formed with a plurality of fluid flow channels 106 associated with microneedles 104. At least one additional element 108 cooperates with substrate 100 so as to together form a structure including a substantially-fixed-volume fluid transfer cell 110 in fluid connection with the plurality of fluid flow channels 106, a fluid pumping cell 112, at least partially enclosed by a flexible wall 114 which can be displaced to vary an internal volume of the fluid pumping cell, and a one-way valve 116 for defining a flow direction between fluid transfer cell 110 and fluid pumping cell 112. As a result of this structure, when the device is deployed with microneedles 104 penetrating into the biological barrier, displacement of flexible wall 114 in a predefined direction causes a change in the internal volume of pumping cell 112, resulting in fluid flow through one-way valve 116 and hence fluid transfer between fluid transfer cell 110 and microneedles 104 via fluid flow channels 106.

Turning more specifically to the examples of FIGS. 11–14, in certain preferred implementations, the structure further includes a second one-way valve 118 for defining a flow direction between the fluid pumping cell 112 and the atmosphere, optionally via a venting cell 120 with a vent 122. The direction of valves 116 and 118 are chosen such that reciprocal displacement of flexible wall 114 may be used to generate net fluid flow between the fluid pumping cell 112 and fluid transfer cell 110. In this case, flexible wall 114 need only exhibit sufficient flexibility to cause very slight volume variations in pumping cell 112, so long as some fluid moves through each valve during each cycle of flexing. Suitable structures can thus be implemented using a relatively thin wall 114 integrally formed as part of an element 108 formed from a second silicon substrate or the like.

For simplicity of presentation, the device for actuating reciprocal displacement (vibration) of flexible wall 114 has been omitted from FIGS. 11–17. According to a first preferred option (shown schematically in a parallel implementation in FIGS. 18 and 19), a piezoelectric actuator 124 is mechanically linked to flexible wall 114, typically by attachment directly thereto, so as to generate vibration of the flexible wall. In this case, the form of an electrode on the actuator may advantageously be patterned in such way as to cause asymmetric vibrations which tend to mix the fluids within the chamber and/or cause directional flow concentration in a manner to increase efficiency of injection of the fluid through the needles. According to a second preferred option (shown schematically in a parallel implementation in FIGS. 20–22), an acoustic vibration generator 126 is employed for generating vibrations of flexible wall 114 remotely via air waves. Although, in some cases, the combination of blood pressure and capillary action alone could be sufficient for sampling applications, the provision of the pumping configurations of the present invention is believed to be advantageous for greater reliability and speed of response.

In preferred implementations, one-way valves 116 and 118 are implemented using micro-electromechanical structures (MEMS). Techniques for forming MEMS flow valves are well known in the art. A description of a number of different MEMS technologies which may be used for the purpose may be found in an article entitled "A Micro Valve Made of PSPI" by Xiaohao Wang et al., DSC-Vol. 66, MEMS (1998), ASME 1998 (pp31–36), which is hereby incorporated by reference.

In the particular example of FIGS. 11–14, the device is configured for withdrawal of fluid across the biological barrier, such as for diagnostic sampling. Thus, one-way valve 116 is configured to allow fluid flow selectively from fluid transfer cell 110 to fluid pumping cell 112.

For diagnostic applications, at least one sensor 128, associated with either fluid transfer cell 110 or fluid pumping cell 112, is configured to generate an output indicative of at least one parameter associated with fluid withdrawn across the biological barrier. Sensor 128 is preferably an integrated structure formed on substrate 100 which can be connected to a local diagnosis system, or can be associated with a communications system which is configured to transmit data associated with the output to a remote site. A system of the latter type will be addressed further below.

The choice of sensor 128 is clearly specific to the intended application. It should be noted, however, that a vast range of on-chip diagnostic sensors are known, starting from the simplest of conductivity sensors and extending up to "micro total analytical systems" (Micro TAS) or "lab on chip" devices.

By way of example, sensor 128 may be chosen from a class of "thermal chemical microsensors" embedded in pumping chamber 112. The micro sensor includes a quantity of an enzyme which reacts with a particular substance to generate or absorb heat. The resulting temperature change is detected such as by a thermistors ceramic layer (e.g. BaO/SrO). She thermistors can have a negative or positive temperature coefficient of resistance (TCR) and cover a typical range of −80 to 350° C. with resistance from 100 to 1 MΩ. The TCR is typically ±5%/° C. and the glass coating makes the thermistor an extremely stable (±0.05° C./yr). A sensor of this type is described in an article entitled "Micro-Sensors—Principles And Applications" by Julian W. Gardner WILEY (1996) pp. 240–241. As an alternative to thermistors, ISFET or MOS capacitors may be used, as described in Garner pp. 236–239.

The following table lists a range of substances which can be measured by this technique, and indicates the corresponding enzyme to be used.

| Analyte | Enzymes |
|---|---|
| Cholesterol | Cholesterol oxidase |
| Glucose | Glucose oxidase (GOx) |
| $H_2O_2$ | Catalase |
| Lactate | Lactate oxidase |
| Urea | Urease |
| Lipids | Lipase |
| Peptides | Trypisn |
| ATP | ATPase |

One particularly important example is the glucose enzyme thermistor which involves a sequence of two reactions. First, the glucose is converted to gluconic acid by GOx and produces $H_2O_2$. Then the $H_2O_2$ reacts to produce water and oxygen. The total change in enthalpy can be measured using two thermistors in which the second one acts as at reference resistors in a Wheatstone bridge arrangement.

An alternative example relates to a patch for minimal invasive diagnosis of Acute Myocardial Infarction (AMI). In this case, blood is tested for an accumulation of cardiac markers such as Myoglobin, Creatine Kinase-MB (CK-MB) and Troponin which are released from dying tissue once damage to the heart has already occurred. This can be done using one or more sensor 128 along the lines of those described above. The extent of the reaction can be detected by measuring the changing resistance in the detector layer or measuring the sensitivity of an ISFET or MOS gate which is in contact with the reactive layer. Here too, the principles of such sensors may be found in the Gamer reference (pp. 236–239). The resistive changes enable quantification of the amount of marker received, and can be transferred to a remote location, such as by the systems to be discussed below, to verify whether a heart attack is in progress. Preferably, two or more of the markers are measured to provide failsafe diagnostic information.

It should be appreciated that such an application is revolutionary in the field of immediate diagnosis of heart attacks. Cardiac marker testing is a standard procedure worldwide for diagnosing patients with chest pain. Currently, such testing is performed exclusively in hospitals, leading to a major delay before positive diagnosis. As an alternative, the present invention offers a remote, minimally invasive device usable without trained personnel which concurrently measures the accumulation of Myoglobin, CK-MB and Troponin in the blood to provide an immediate indication of whether chest pain is due to heart damage. This could provide immediate identification of AMI, thereby helping health care staff to assess the urgency of a situation, and providing the correct initial treatment.

Figure 15:
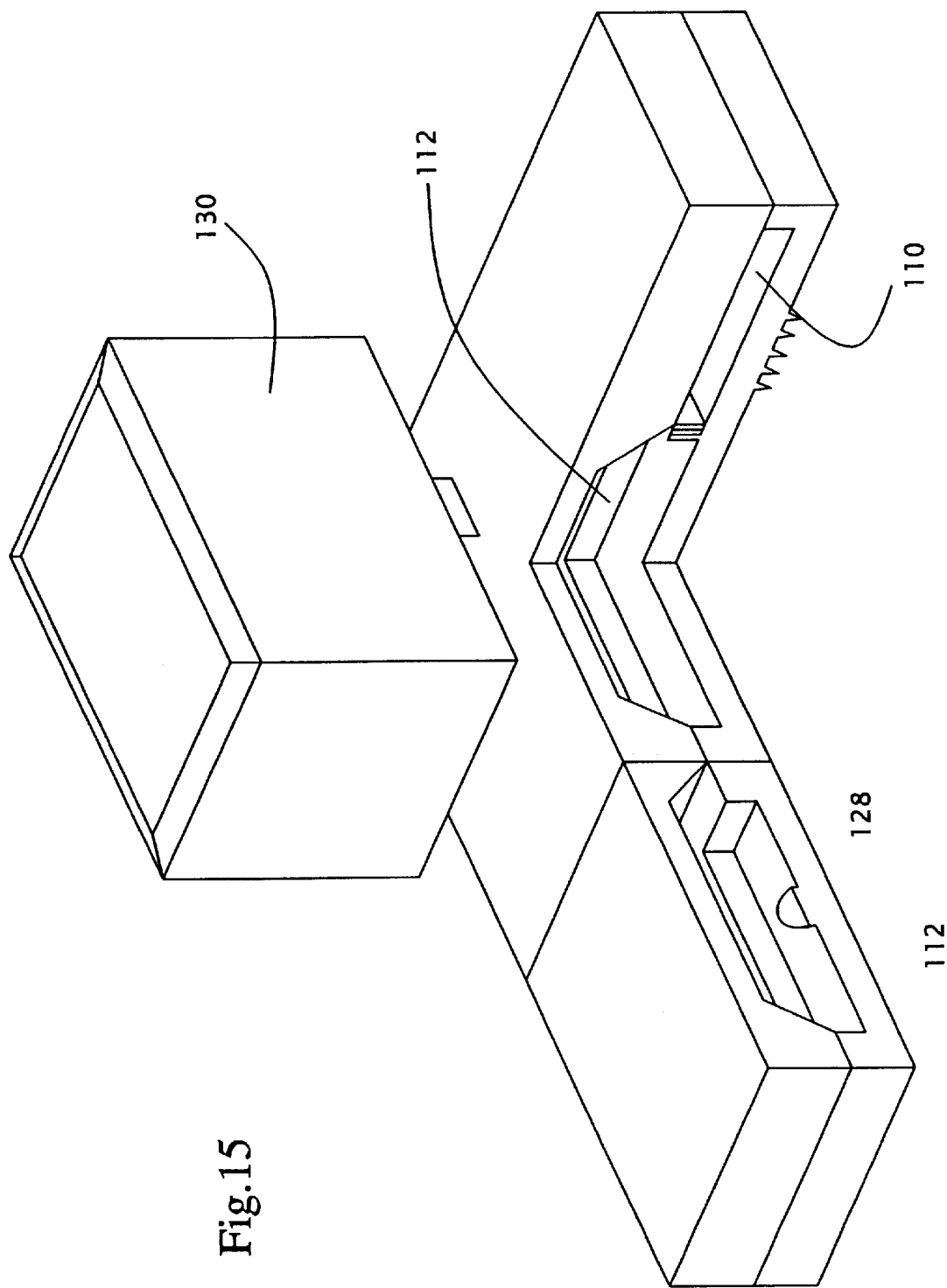
FIG. 15 is a schematic partially cut-away isometric view of a second device, constructed and operative according to the teachings of the present invention, employing microneedles for delivery of fluid across a biological barrier.
Figure 16:
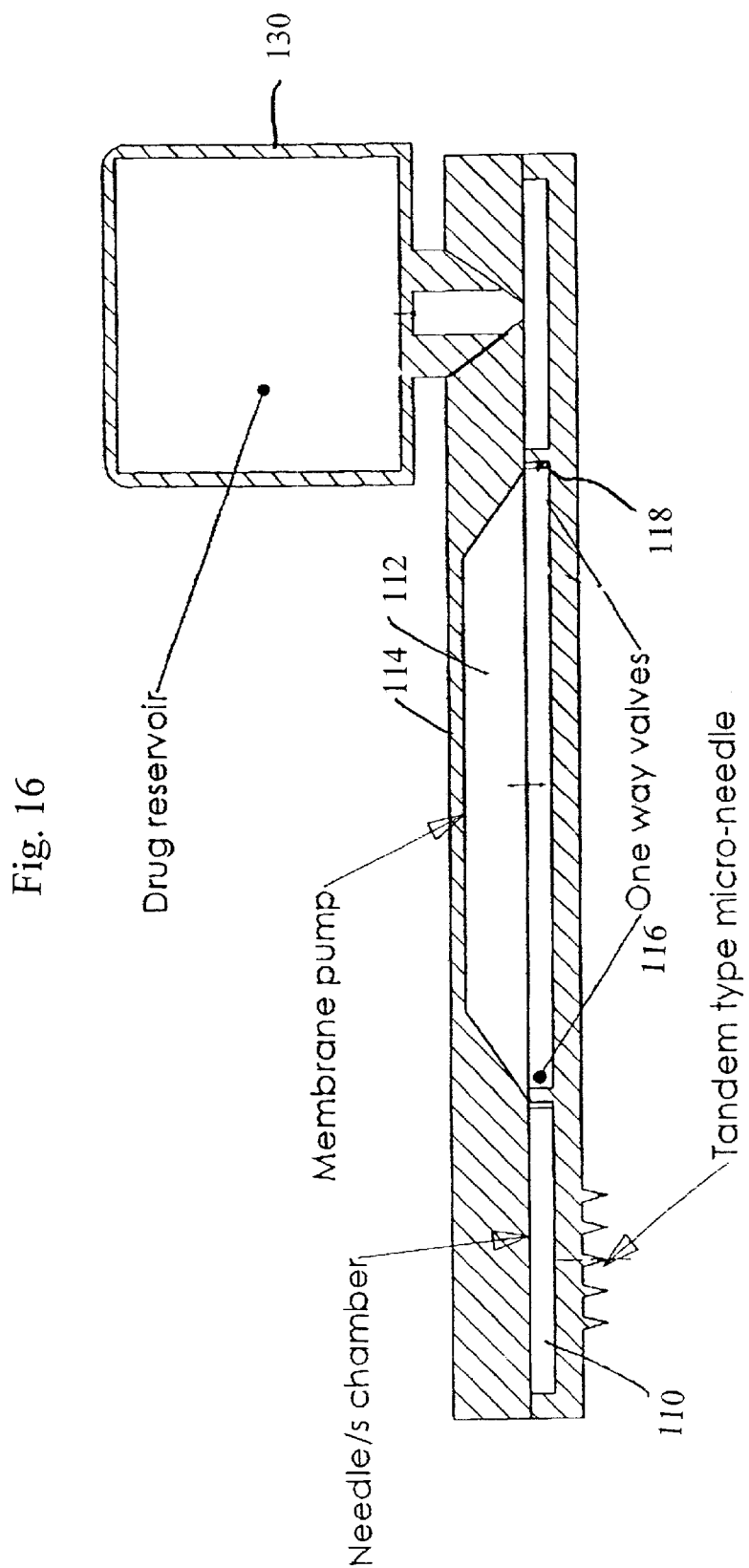
FIG. 16 is a schematic cross-sectional view through the device of FIG. 15.

Turning now to FIGS. 15 and 16, there is shown an alternative version of the device, in this case configured for delivery of fluid across the biological barrier. In this case, valve 116 is configured to allow fluid flow selectively from fluid pumping cell 112 to fluid transfer cell 110.

For supply of fluid, such as a drug to be delivered into the body, device preferably also includes a fluid reservoir 130 connected to pumping cell 112 via second one-way valve 118 configured to define a flow direction from reservoir 130 to fluid pumping cell 112. As a result of this structure, reciprocal displacement of flexible wall 114 generates net fluid flow between fluid reservoir 130 and fluid transfer cell 110 via fluid pumping cell 112.

Reservoir 130 is preferably configured to avoid producing a significant back-pressure against operation of the pumping cell. This may most readily be achieved by using a flexible or otherwise variable-volume reservoir.

It should be appreciated that the configuration described allows very precise control over the volume of fluid delivered. Specifically, after initial priming of the device, the volume transferred by the pumping configuration is the product of the volume change $\Delta V$ of pumping cell 112 between the extreme positions of flexible wall 114 and the number of cycles n through which it is moved. Thus by providing an actuator with known characteristics, such as the piezoelectric actuator or acoustic vibration generator mentioned above, it is possible to deliver a precisely metered quantity of fluid by operating the actuator for a corresponding time period. For drug delivery applications, this may be manually controlled, controlled by a preprogrammed electronic control unit (not shown) or remotely controlled by use of a communications system associated with the actuator and configured to be responsive to dosage data received from a remote site. In each case, the actuator is actuated to deliver a required dosage of fluid across the biological barrier.

Figure 17:
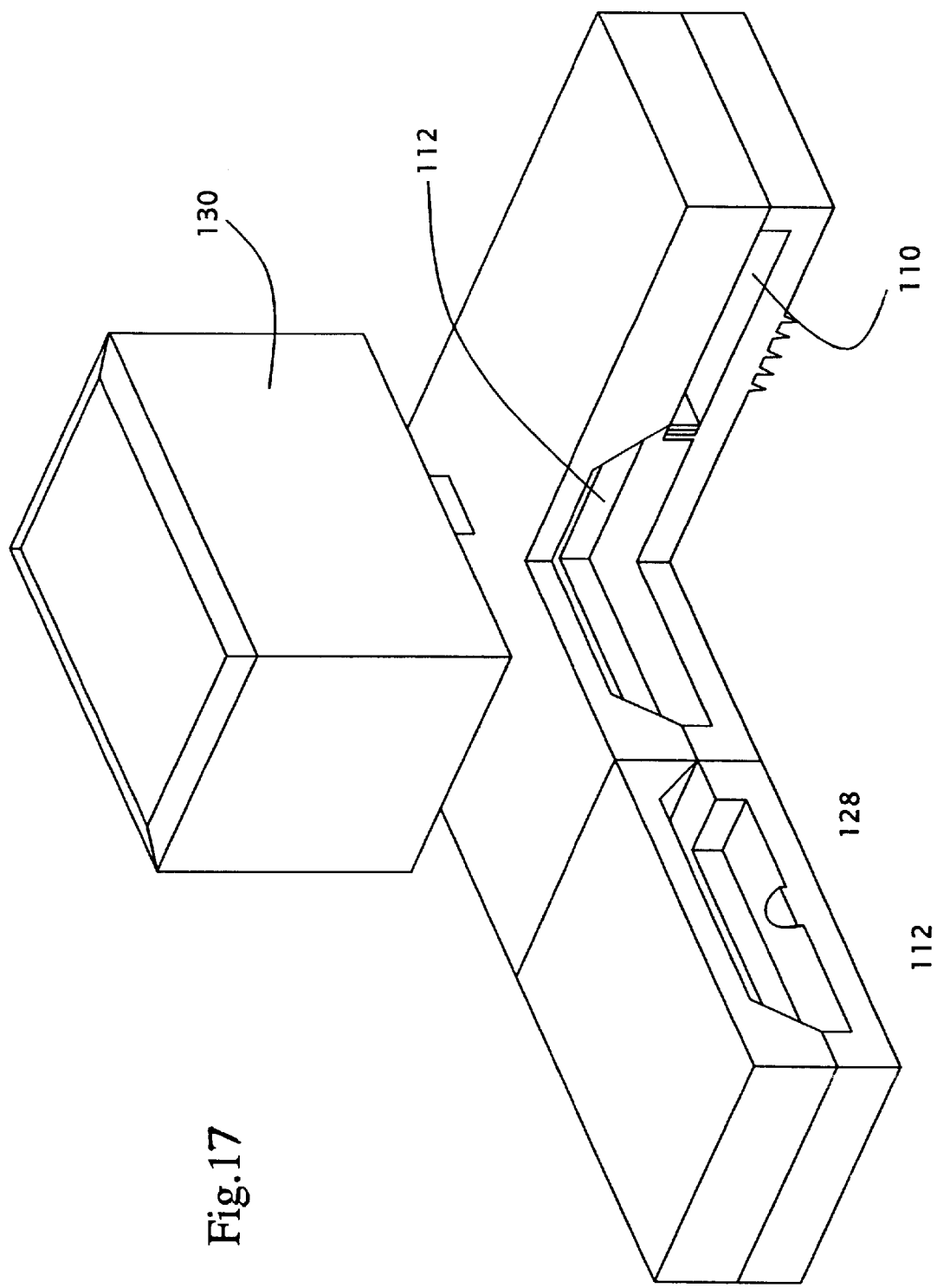
FIG. 17 is a schematic isometric view of a diagnostic sampling and drug delivery device formed from a combination of the devices of FIGS. 11 and 15.
Figure 18:
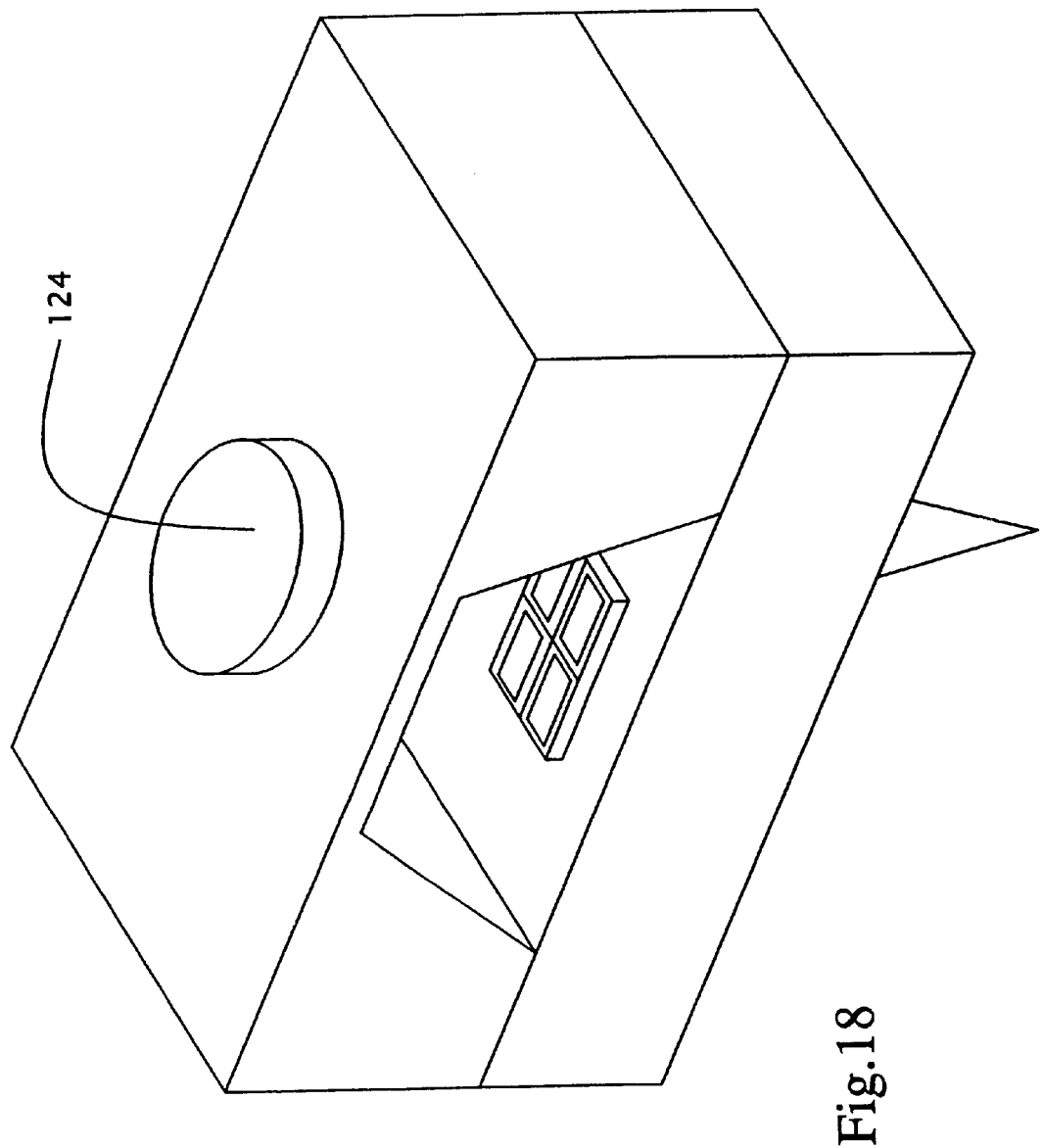
FIG. 18 is a schematic partially cut-away isometric view of a fourth device, constructed and operative according to the teachings of the present invention, employing microneedles for transfer of fluid across a biological barrier.
Figure 19:
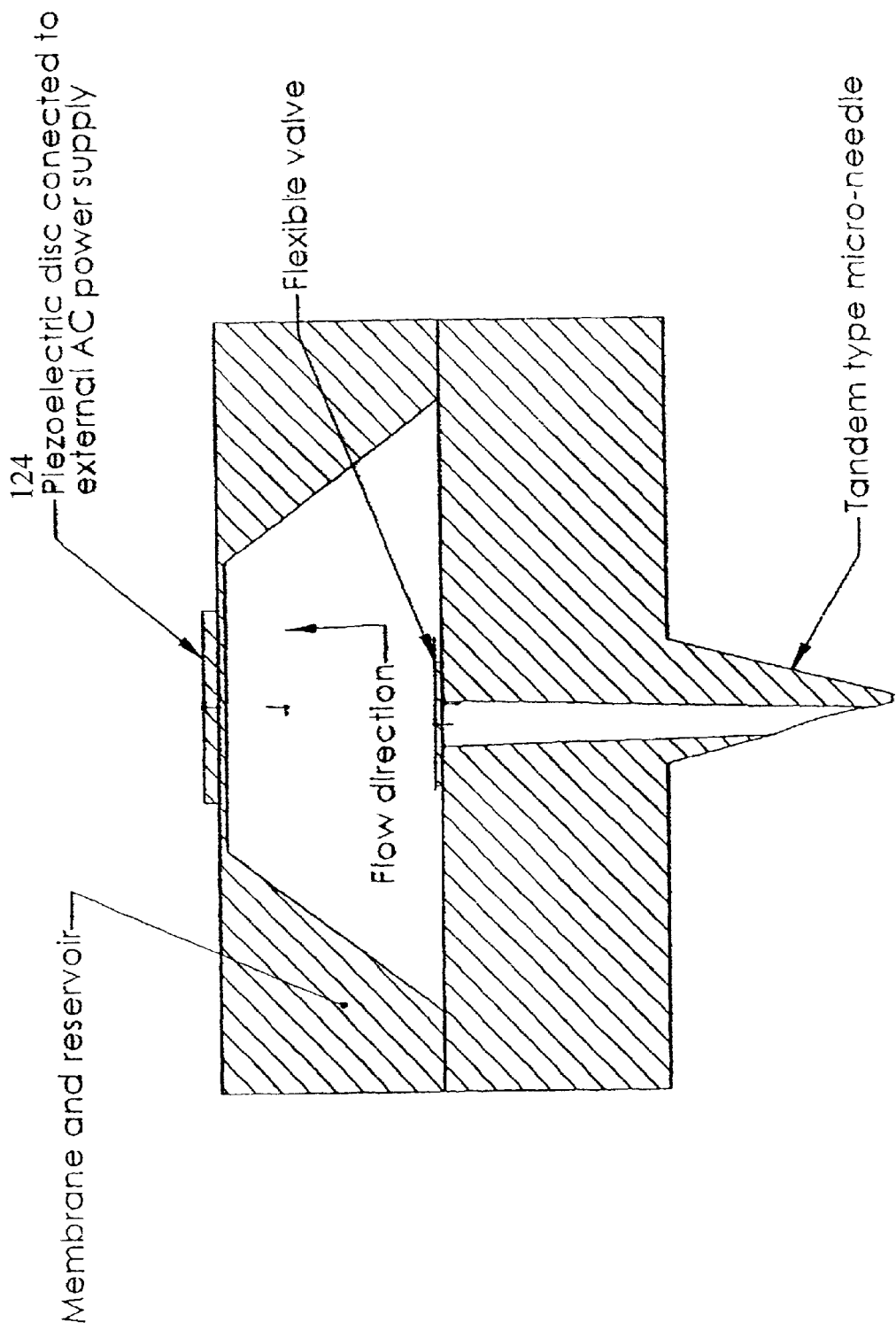
FIG. 19 is a schematic cross-sectional view through the device of FIG. 18.

Turning briefly to FIG. 17, it will be appreciated that the devices of the present invention may readily be constructed to have both fluid withdrawal and delivery capabilities. This possibility is particularly useful for closed loop self-treatment or remote healthcare applications where a single device can be used to derive diagnostic data and provide treatment.

Figure 11:
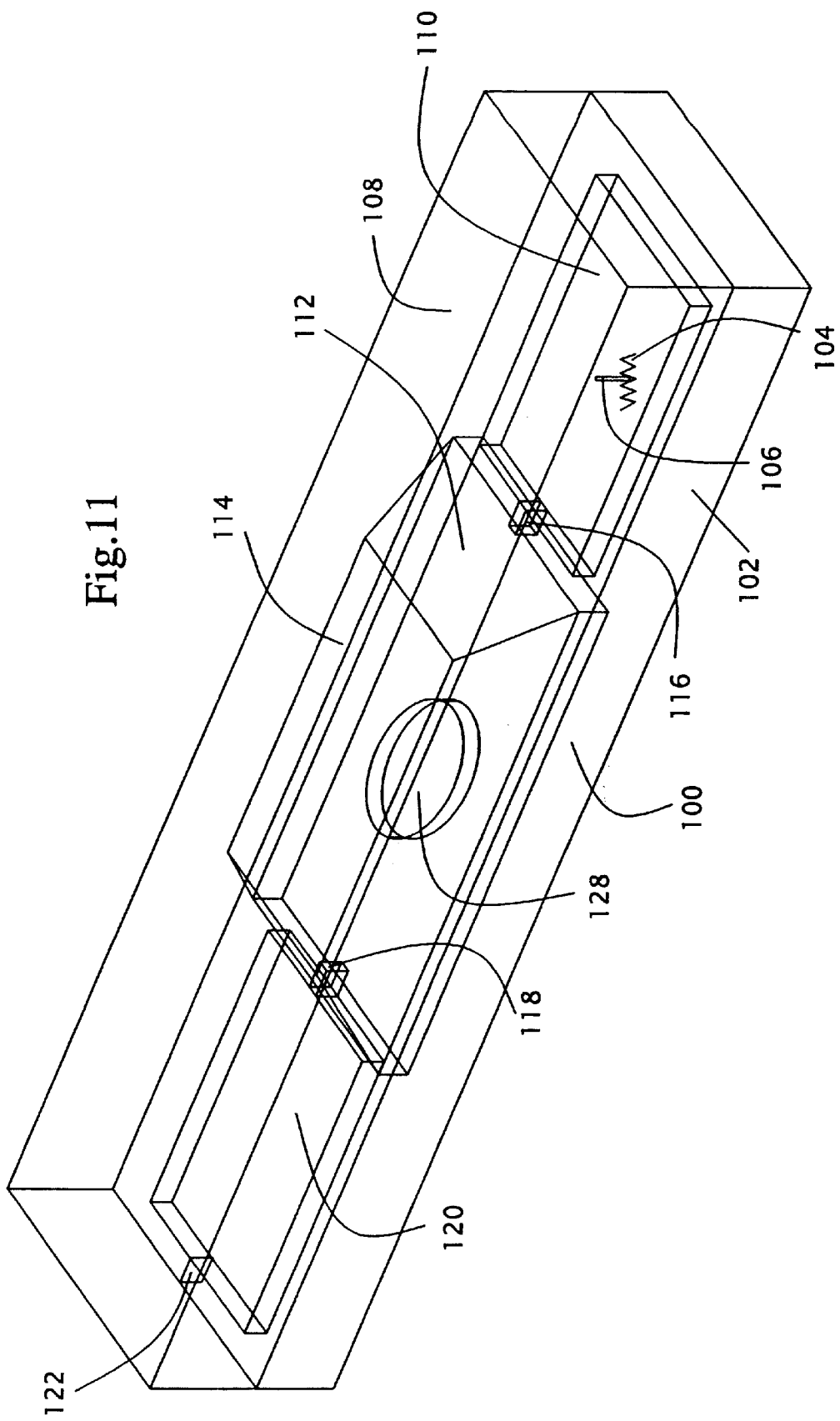
FIG. 11 is a schematic partially cut-away isometric view of a first device, constructed and operative according to the teachings of the present invention, employing microneedles for sampling and analysis of fluid withdrawn across a biological barrier.
Figure 12:
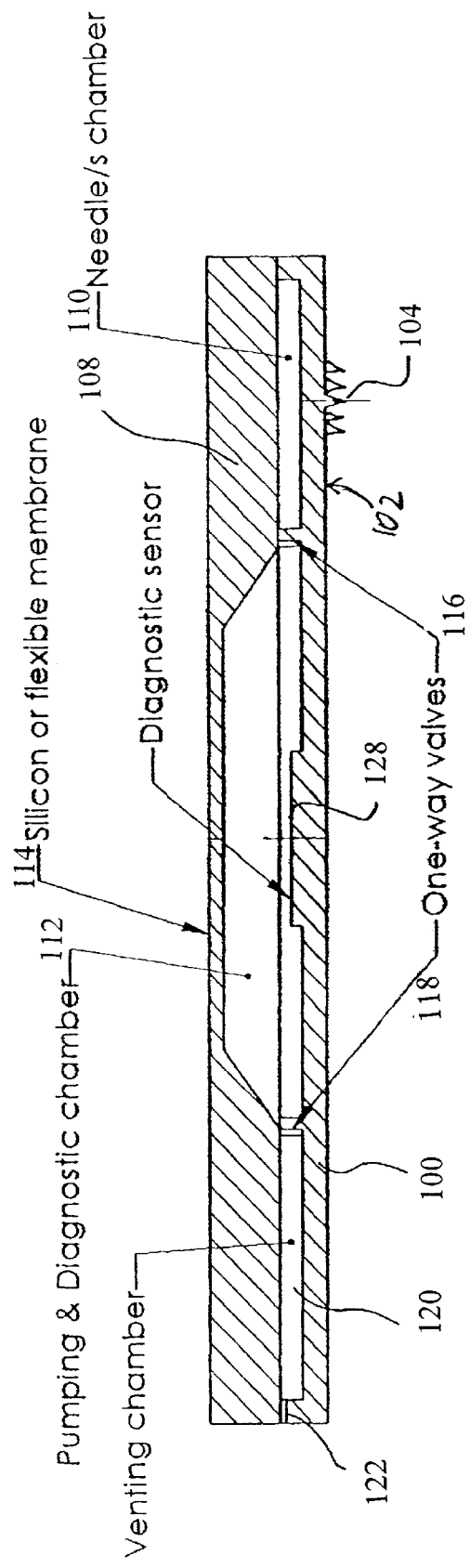
FIG. 12 is a schematic cross-sectional view through the device of FIG. 11.

Structurally, the device shown here is implemented as a side-by-side combination of the devices of FIGS. 11 and 15, typically integrally formed on a single wafer. It should be understood, however, that various components of the device may optionally be combined. By way of example, the microneedle structure of FIG. 9 opens up a possibility of providing separate flow paths for fluid delivery and withdrawal using a single set of microneedles.

Although the possibility of remote diagnosis and immediate treatment in the absence of trained medical personnel raises problems of safety, such systems are thought to be feasible for a large number of applications in which a pre-diagnosed condition requires drug therapy as a function of physiological parameters. A prime example of such an application is insulin-dependent diabetes in which a closed-loop system could monitor blood glucose levels and deliver an appropriate dosage of insulin. The entire process of measurement and drug delivery can be performed in a substantially painless minimally invasive manner.

Another group of possible closed-loop remote health care applications relates to situations where the priority of rapid treatment outweighs considerations of a possibly mistaken treatment. Examples of such applications are in the field of poisoning in cases where a non-dangerous antidote exists.

Figure 20:
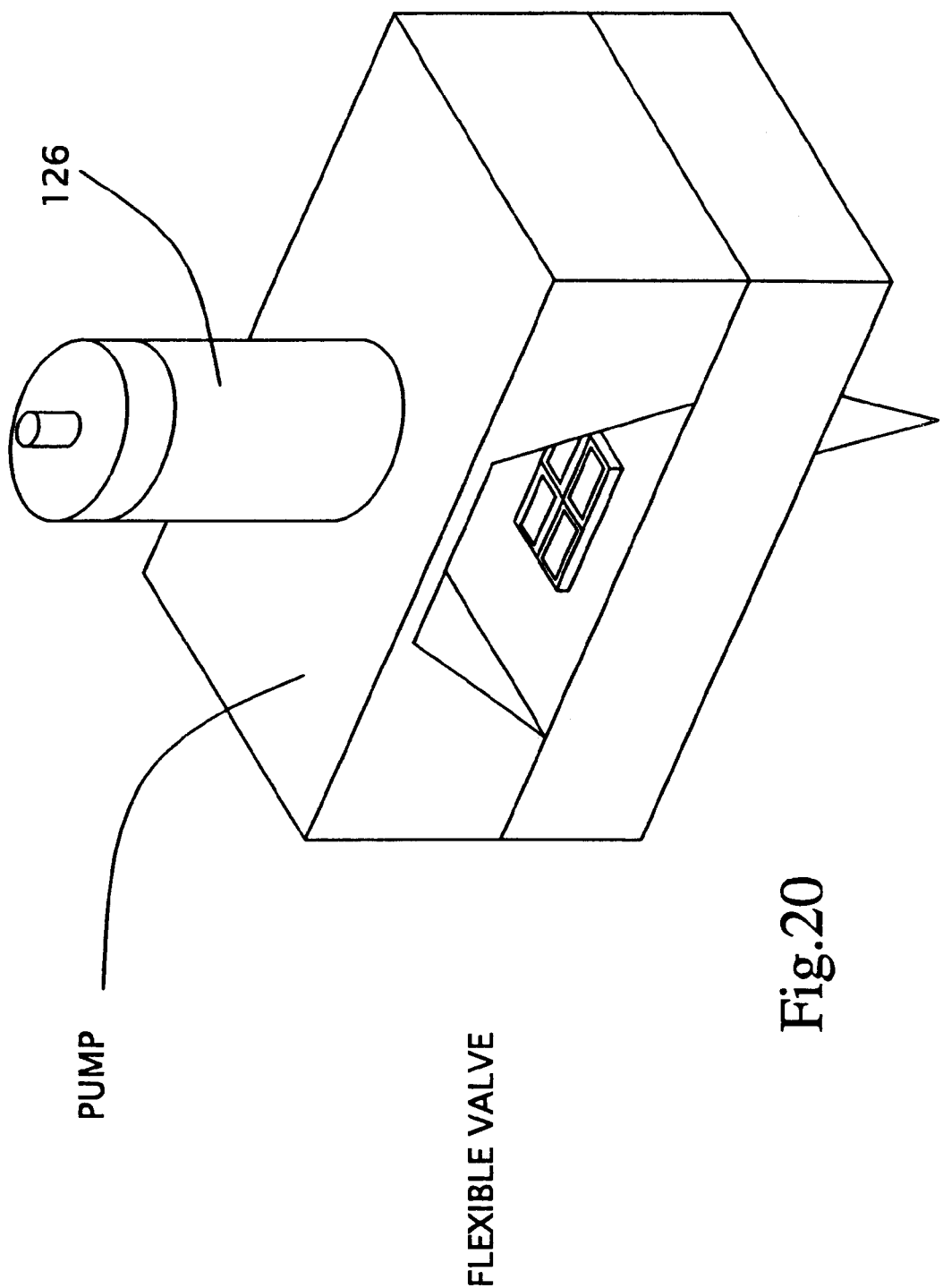
FIG. 20 is a schematic cut-away isometric view of a fifth device, constructed and operative according to the teachings of the present invention, employing microneedles for transfer of fluid across a biological barrier.
Figure 21:
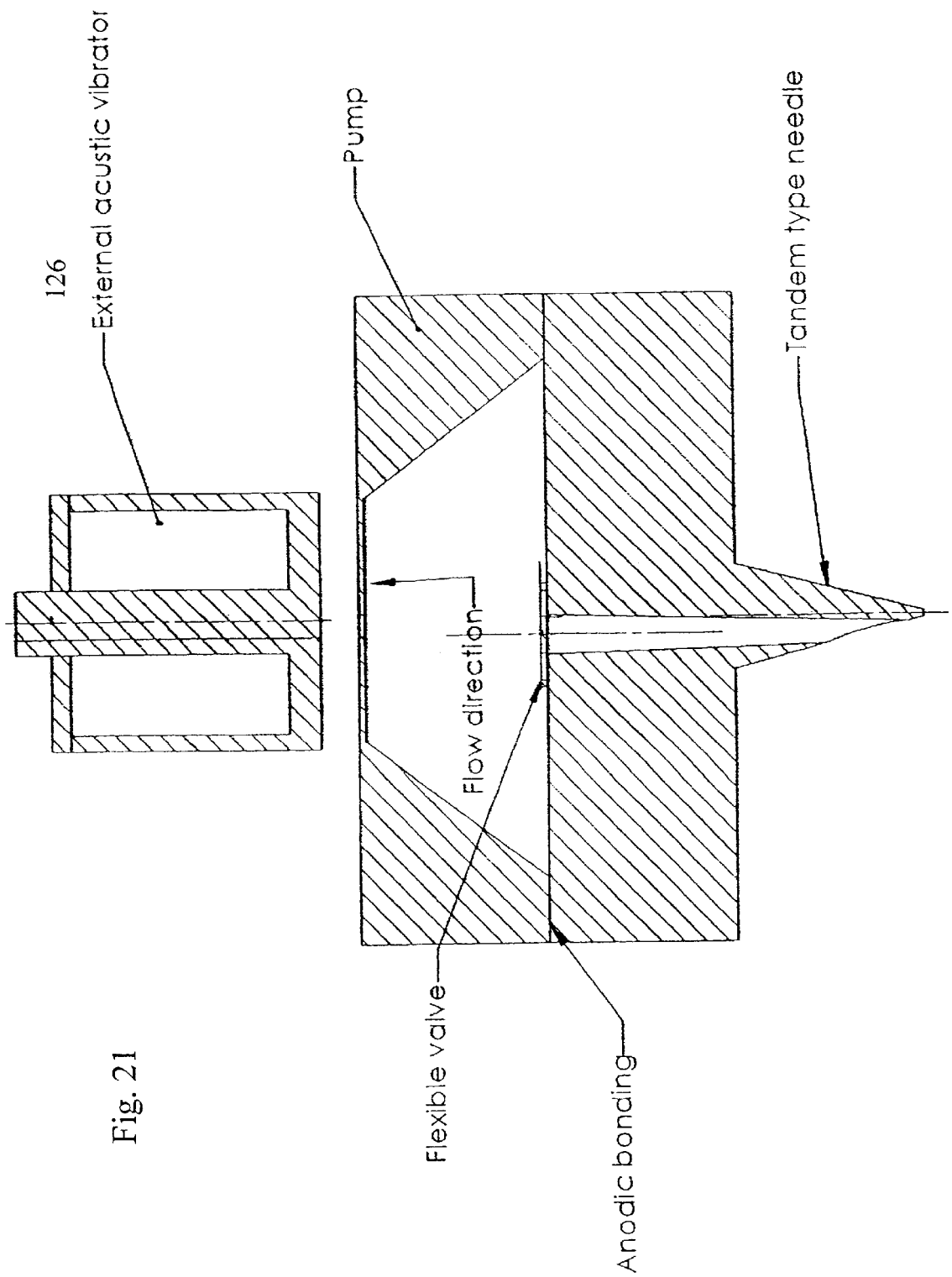
FIG. 21 is a schematic cross-sectional view through the device of FIG. 20.
Figure 22:
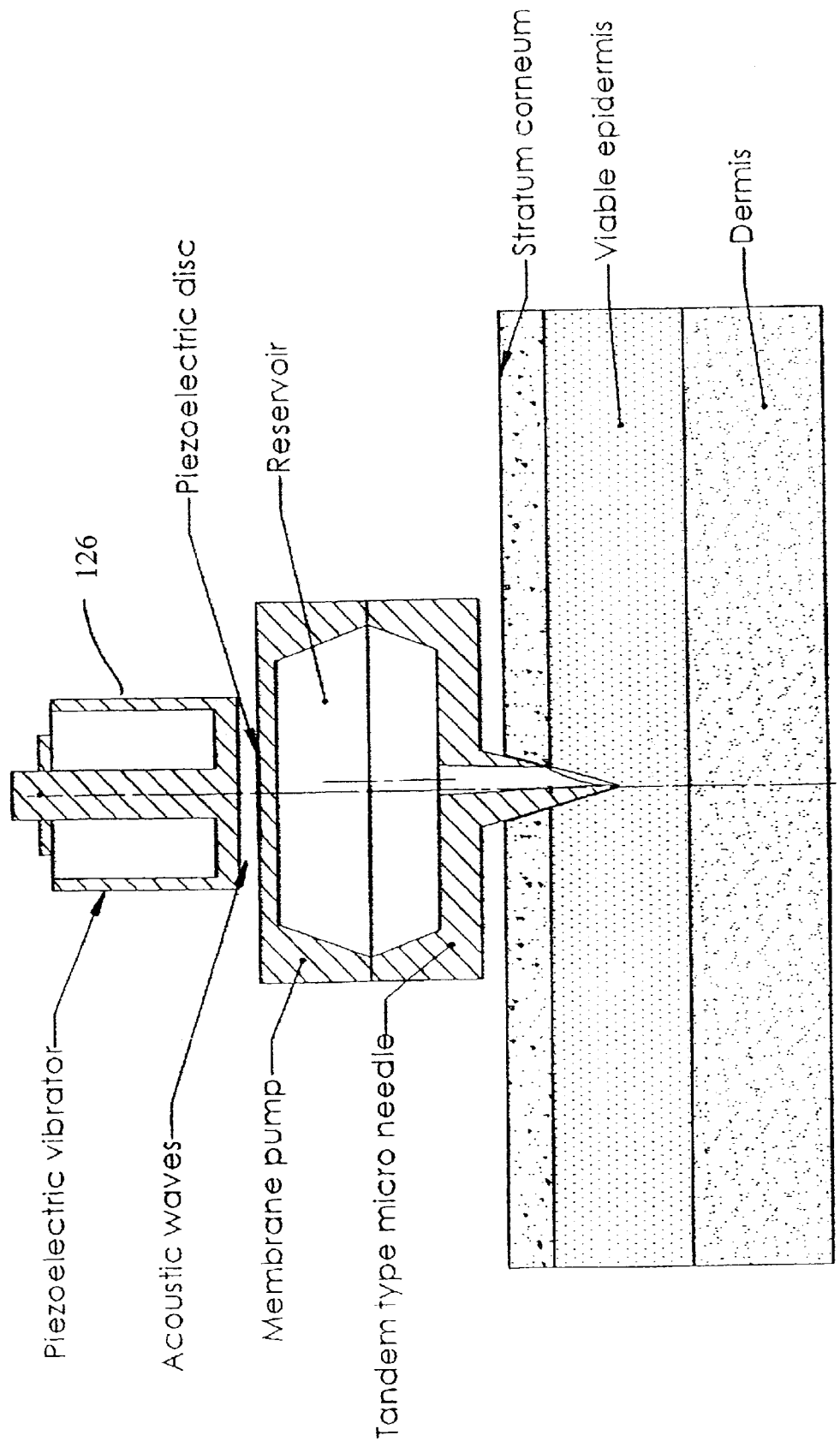
FIG. 22 is a schematic cross-sectional view illustrating the use of the device of FIG. 20 for transferring fluid across a biological barrier.
Figure 23A:
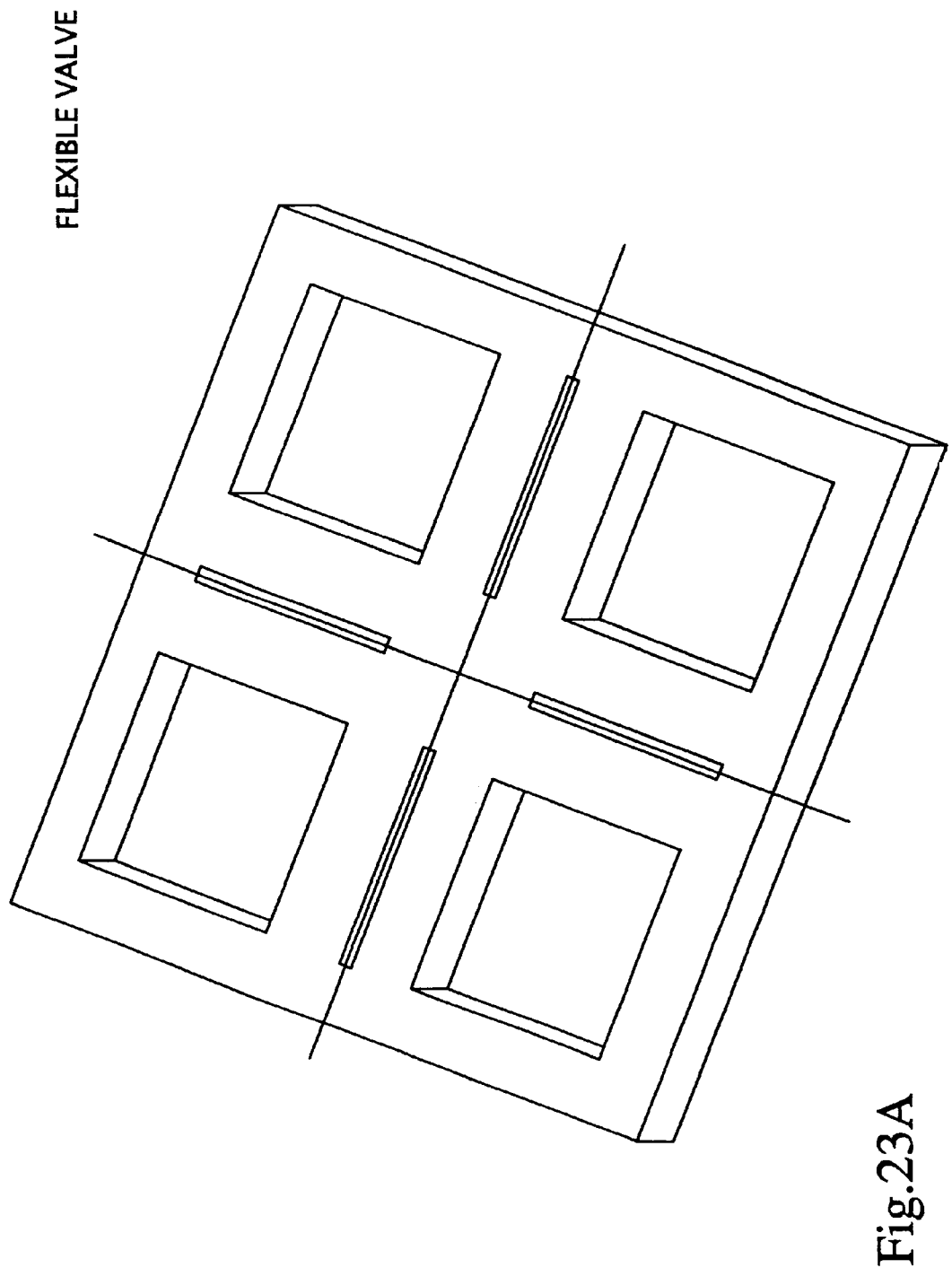
FIGS. 23A and 23B are schematic isometric views of valve elements for use in the devices of FIGS. 18 and 20 for withdrawal and delivery applications, respectively.
Figure 23B:
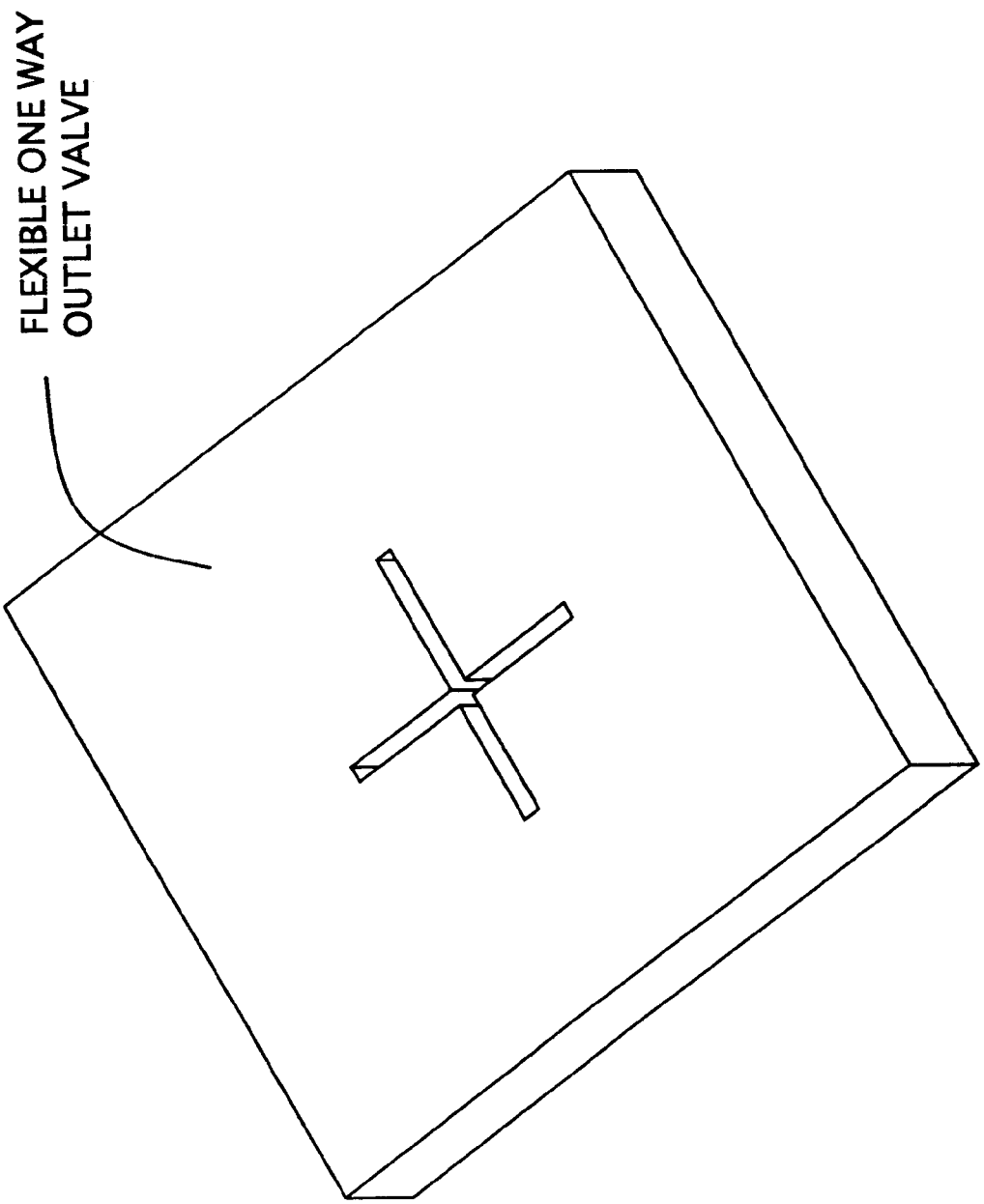

Turning now briefly to FIGS. 18–23, these show schematically alternative device configurations actuated either by a piezoelectric actuator 124 (FIGS. 18 and 19) or remotely by an acoustic vibration generator 126 (FIGS. 20–22). These devices also exemplify an alternative valve structures in which a polymer valve element is deployed over an appropriately shaped opening to the fluid flow conduit through the microneedles. FIG. 23A shows an example of the form of the valve element for fluid withdrawal, while FIG. 23B shows an alternative form for positive pressure delivery. In each case of fluid withdrawal, a second venting valve (not shown) is provided, typically in an adjacent chamber. The function and operation of these valves will be clearly understood by one ordinarily skilled in the art from the discussion of the PSPI valve of the aforementioned Wang et al. reference.

Figure 24:
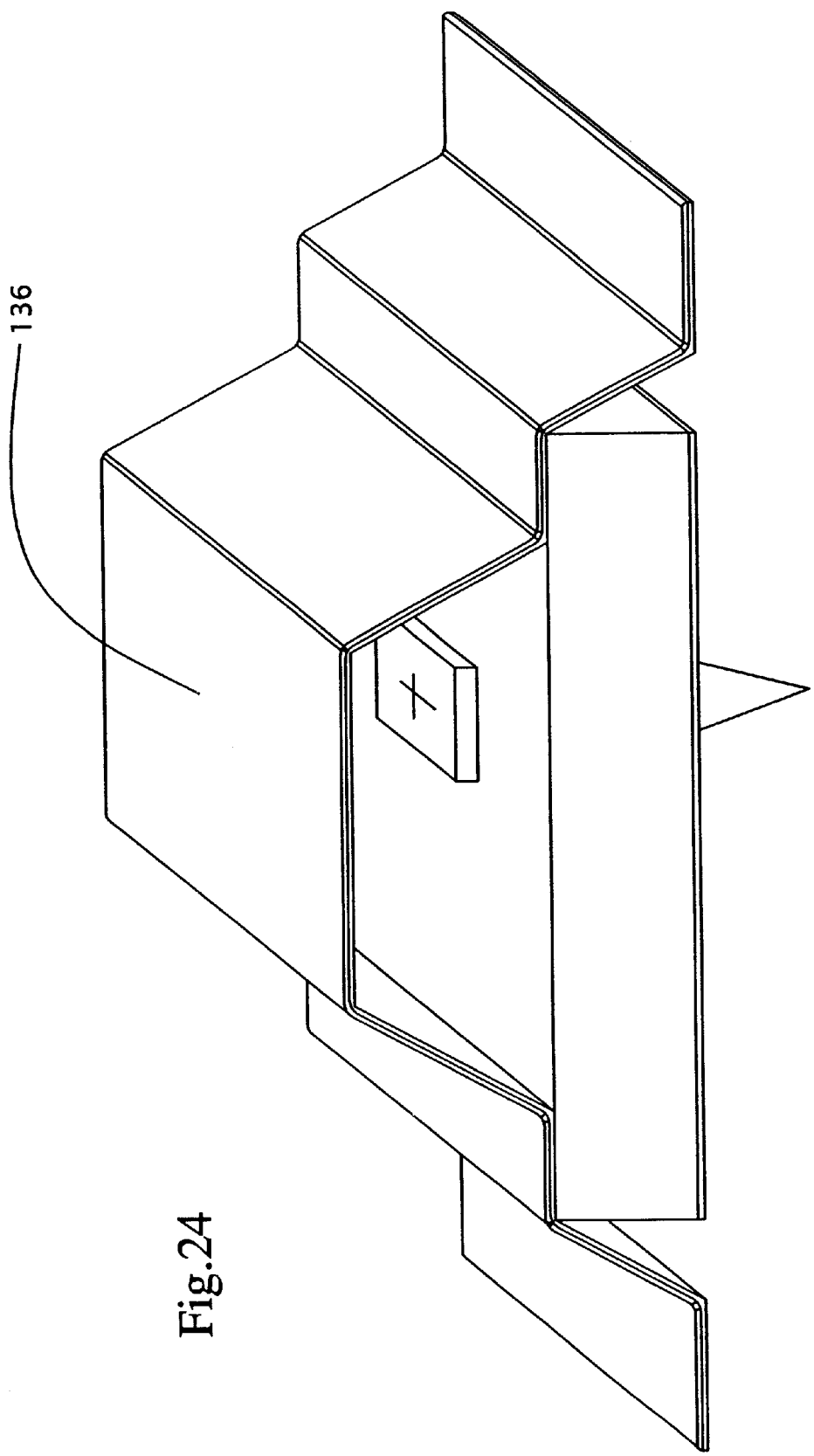
FIG. 24 is a schematic cut-away isometric view of a sixth device, constructed and operative according to the teachings of the present invention, employing microneedles for transfer of fluid across a biological barrier.
Figure 25:
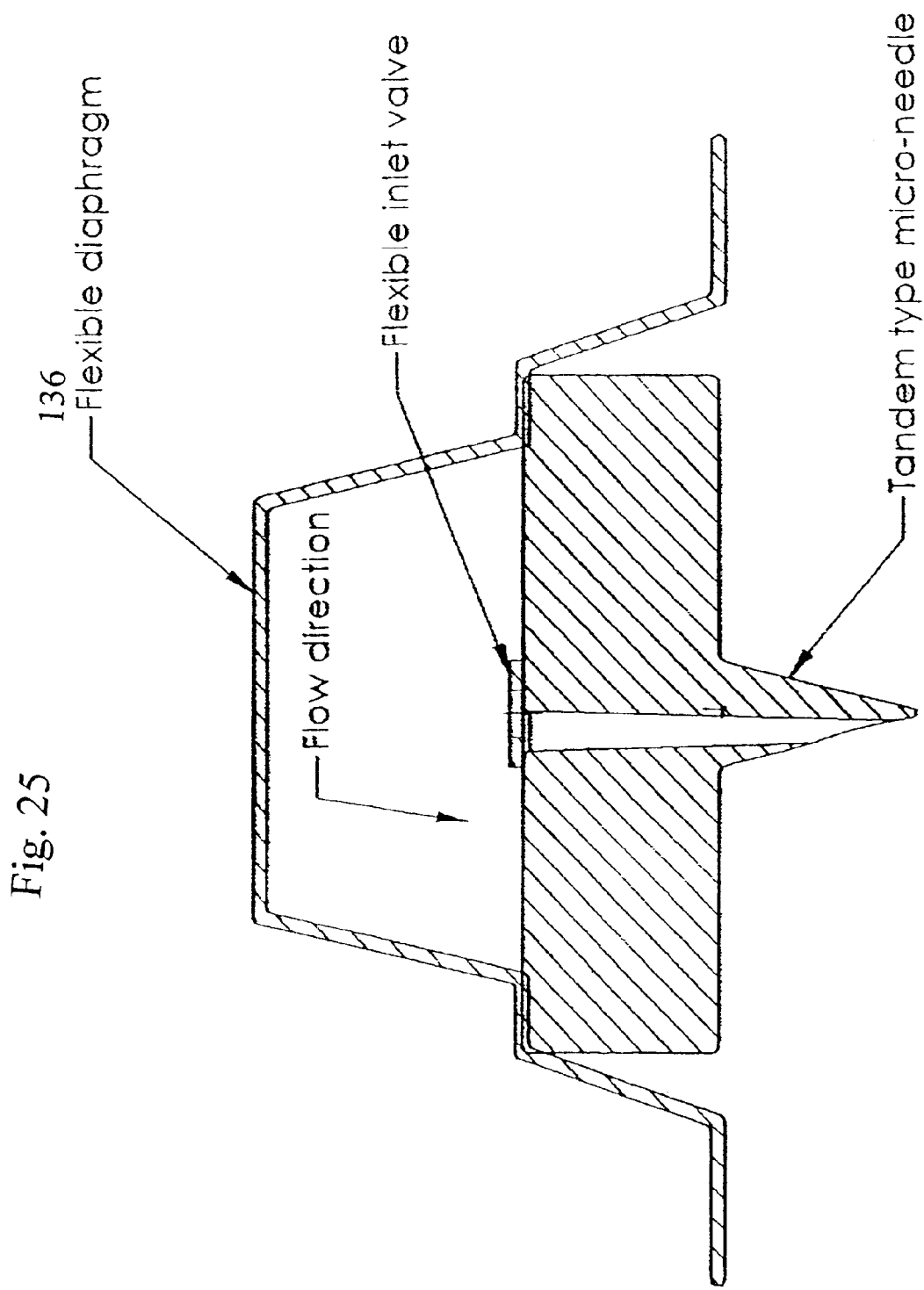
FIG. 25 is a schematic cross-sectional view through the device of FIG. 24.

Turning now to FIGS. 24 and 25, there is shown an alternative device configuration for drug delivery in which a flexible wall 136 is configured to be manually depressible. This implementation requires only a single valve of the type illustrated in FIG. 23B and is particularly suited to applications in which highly accurate dosage is not critical.

Structurally, the device can advantageously be implemented with flexible wall 136 formed primarily from silicon rubber. This may conveniently be formed during production of the wafer structure using spin coating technology. Spin coating is a technique known in MEMS and IC production for coating of a photo-resist layer on the top surface (for further discussion, see "The challenges of microsystem technology: FSRM Training in MST", J. Flutman et al., 1999). In this application, the technique may be used for coating silicon rubber over a sacrificial layer formed over the wafer surface. After coating, the sacrificial layer is removed, leaving the silicon rubber layer as a flexible reservoir wall. Alternatively, other polymer materials may be used, such as polyamide.

As mentioned earlier, the devices of the present invention are advantageously, although not necessarily, implemented using the principles of microneedles structures described above with reference to FIGS. 2–10.

Remote Healthcare Systems

Figure 26:
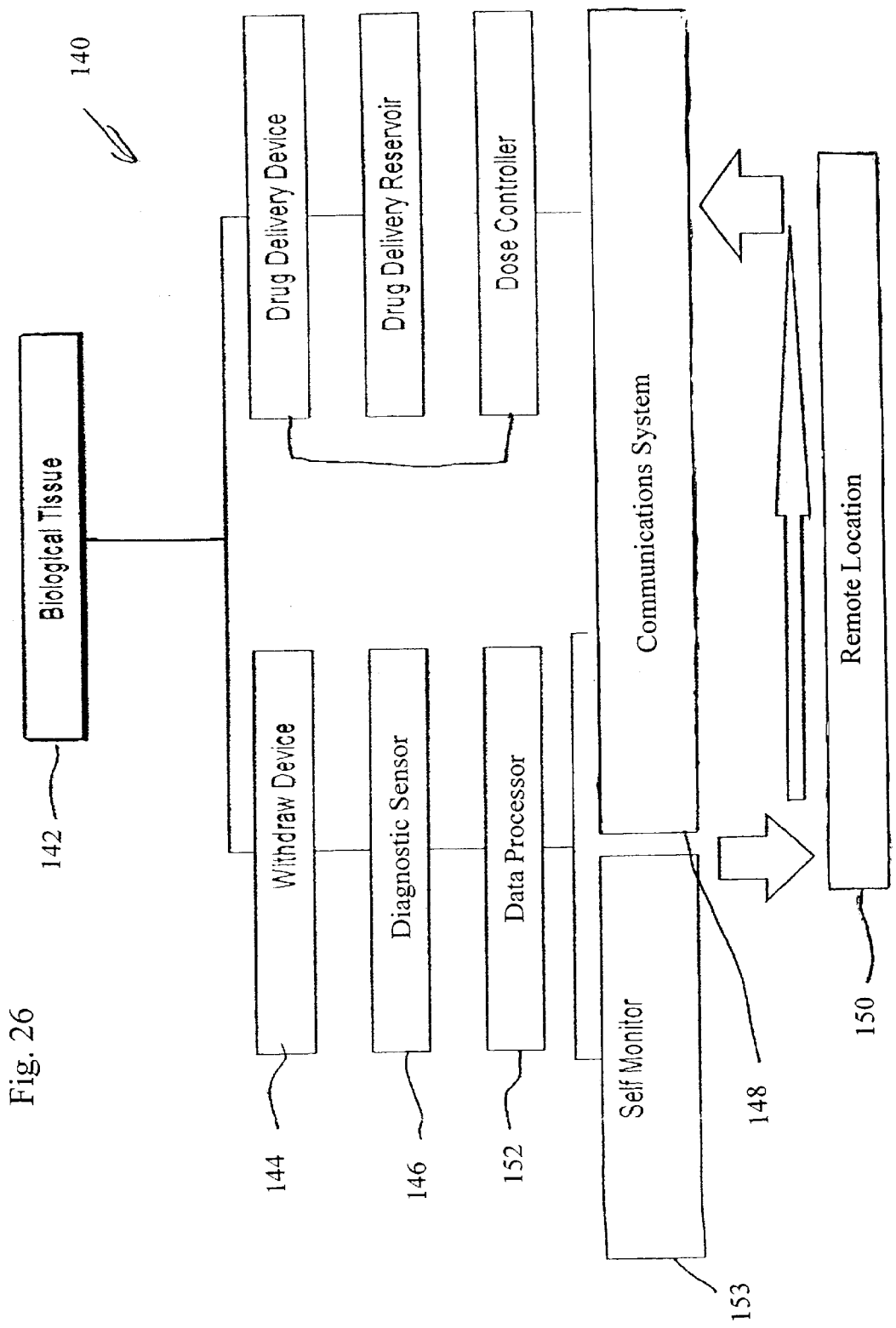
FIG. 26 is a block diagram illustrating a system for remote diagnosis and/or treatment according to the teachings of the present invention.

Turning now to FIGS. 26 and 27, the present invention also provides a system, generally designated 140, constructed and operative according to the teachings of the present invention, for remote diagnosis based on sampling of fluid withdrawn from tissue 142 through a biological barrier.

Generally speaking, for remote diagnosis applications, system 140 includes a sampling device 144 for pressing against the biological barrier to withdraw fluid therethrough. At least one sensor 146, associated with sampling device 144, is configured to generate an output indicative of at least one parameter associated with fluid withdrawn across the biological barrier. A communications system 148, associated with sensor 146, is configured to transmit data associated with the sensor output to a remote site 150.

Sampling device 144 is minimally invasive, being configured to penetrate less than 1 mm into the tissue. Preferably, the device is a microneedle-based device, most preferably of the types described above and using microneedle structures as described above.

Depending upon the type of sensor used, an additional data processor 152 may be provided to process the output of sensor 146 to generate the data for transmission. Typical processing steps include A/D conversion and derivation of various quantitative parameters from the output, either by calculation or by use of look-up tables. An output device, such as a graphic display 153 may optionally be added to provide instruction and/or information to the user.

Data processor 152 and communications system 148 may readily be implemented using a wide range of hardware and accompanying software as will be self evident to one ordinarily skilled in the art. By way of one non-limiting example, FIG. 27 shows one particular implementation in which a portable computer 154 is used in combination with a cellular communications device 156. A/D conversion may be performed by a dedicated D/A input converting PCMCIA card 158 to which the sensor output is connected. Computer 154 may be connected to the communications device via a standard PCMCIA modem 160 compatible with the GSM system. Alternatively, a conventional telephone network, or other communications network, may be used.

Also shown in FIG. 27 is an example of a mobile implementation of the remote part of the communications system. Here, the same components may be used, namely, cellular communications device 156, PCMCIA modem 160 and portable computer 154. The A/D converter is not required. In this case, the function of the computer is to display the diagnostic data in a suitable format for analysis by a medical professional. Clearly a fixed remote station, hard-wired to a telephone communications system or computer network could equally be used.

Returning now to FIG. 26, it will be appreciated that system 140 may alternatively, or additionally, provide facilities for remote administration of one or more drug. In this case, communications system 148 transfers received dosage information to a dose controller 162 which actuates a drug delivery device 164 to deliver a required quantity of a drug from a reservoir 166 into the tissue 142. Here too, device 164 is a minimally invasive device which penetrates into the tissue less than 1 mm, and is preferably a microneedle-based device according to the principles of devices and microneedles described above. Dose controller 162 may also be implemented using portable computer 154 as illustrated in FIG. 27.

It will be appreciated that the above descriptions are intended only to serve as examples, and that many other embodiments are possible within the spirit and the scope of the present invention.

What is claimed is:

1. A device for the transport of fluids through a biological barrier, the device comprising:
   (a) a substrate defining a substantially planar front face of the device;
   (b) a plurality of microneedles projecting from said substantially planar front face, each of said microneedles having a maximum width dimension measured parallel to said front face of no more than about 400 μm and a maximum height dimension measured perpendicular to said front face of no more than about 2 mm; and
   (c) a conduit associated with each of said microneedles and extending through at least part of said substrate, each of said conduits being configured to provide a fluid flow path for transport of fluid through a hole in the biological barrier formed by the corresponding microneedle, wherein each of said microneedles is formed as a conical pyramid having a first conical angle and terminating at an apex, and wherein said conduit is formed as a bore intersecting said conical pyramid not at said apex.

2. The device of claim 1, wherein at least an outer surface of said microneedles is formed from metallic material.

3. The device of claim 1, wherein at least an outer surface of said microneedles is formed from a super-elastic alloy.

4. The device of claim 1, wherein each of said microneedles has a maximum height dimension of no more than about 200 μm.

5. The device of claim 1, wherein said plurality of microneedles is implemented as a two-dimensional array including at least 20 microneedles.

6. A device for the transport of fluids through a biological barrier, the device comprising:
   (a) a substrate having first and second parallel outward-facing surfaces;
   (b) a plurality of bores extending into said substrate from said first surface, each of said bores being substantially symmetrical about a central bore-axis; and
   (c) a plurality of conical projections projecting from said second surface, each of said conical projections being substantially symmetrical about a central cone-axis,
   (d) wherein said bores and said conical projections are configured such that each of said bores intersects an external surface of a corresponding one of said conical projections, said bore-axis and said cone-axis being non-coincident.

7. The device of claim 6, wherein each of said conical projections terminates at an apex, each of said bores being configured to intersect said corresponding conical projection without removing said apex.

8. The device of claim 6, further comprising a layer of metallic material deposited over at least said conical projections.

9. The device of claim 6, further comprising a layer of a super-elastic alloy deposited over at least said conical projections.

10. The device of claim 6, further comprising:
    (a) a plurality of hollow elements, each hollow element being deployed substantially concentrically around, and slightly spaced from, a corresponding one of said conical projections so as to define an annular passageway extending between said hollow element and said conical projection along part of the height of said conical projection; and
    (b) at least one fluid flow channel associated with said substrate and in fluid communication with each of said annular passageways for supplying fluid to said annular passageways.

11. A device for the delivery of fluids through a biological barrier, the device comprising:
    (a) a substrate with a plurality of microneedles projecting therefrom, each of said microneedles having a maximum width dimension of no more than about 400 μm and a maximum height dimension of no more than about 2 mm;
    (b) a plurality of hollow elements, each hollow element being deployed substantially concentrically around, and slightly spaced from, a corresponding one of said microneedles so as to define an annular passageway extending between said hollow element and said microneedle along part of the height of said microneedle; and
    (c) at least one fluid flow channel associated with said substrate and in fluid communication with each of said annular passageways for supplying fluid to said annular passageways.

12. The device of claim 11, wherein said plurality of hollow elements are formed as part of a substantially continuous layer overlying said substrate, and wherein at least part of said at least one fluid flow channel passes between said substrate and said substantially continuous layer.

13. The device of claim 12, Wherein said substantially continuous layer is formed primarily from metallic material.

14. The device of claim 12, wherein said substantially continuous layer is formed primarily from a super-elastic alloy.

* * * * *

UNITED STATES PATENT AND TRADEMARK OFFICE
CERTIFICATE OF CORRECTION

PATENT NO.    : 6,558,361 B1
DATED         : May 6, 2003
INVENTOR(S)   : Yeshurun It is certified that error appears in the above-identified patent and that said Letters Patent is hereby corrected as shown below:

<u>Title page,</u>
Insert -- Item [30] Foreign Application Priority Data
March 9, 2000 (IL) ................................ 134997

Signed and Sealed this

Twenty-first Day of October, 2003

JAMES E. ROGAN
*Director of the United States Patent and Trademark Office*